(12) United States Patent
Matsuda et al.

(10) Patent No.: US 9,539,209 B2
(45) Date of Patent: Jan. 10, 2017

(54) VACCINE FOR MYCOPLASMA INFECTION

(75) Inventors: Kazuhiro Matsuda, Tokyo (JP); Koji Ichiyama, Tokyo (JP); Sachie Matsuda, Tokyo (JP); Yuko Sasaki, Tokyo (JP); Yoshichika Arakawa, Aichi (JP); Ryo Harasawa, Morioka (JP); Yoshihiro Nishida, Matsudo (JP); Norio Katayama, Sakura (JP); Yasuo Endo, Miyagi (JP); Nobuo Nomura, Tokyo (JP)

(73) Assignees: NATIONAL INSTITUTE OF INFECTIOUS DISEASES, Tokyo (JP); M BIO TECHNOLOGY INC., Tokyo (JP)

(*) Notice: Subject to any disclaimer, the term of this patent is extended or adjusted under 35 U.S.C. 154(b) by 1250 days.

(21) Appl. No.: 13/376,009

(22) PCT Filed: Jun. 4, 2010

(86) PCT No.: PCT/JP2010/003732
§ 371 (c)(1),
(2), (4) Date: Feb. 3, 2012

(87) PCT Pub. No.: WO2010/140377
PCT Pub. Date: Dec. 9, 2010

(65) Prior Publication Data
US 2012/0135067 A1 May 31, 2012

(30) Foreign Application Priority Data

Jun. 4, 2009 (JP) ................................. 2009-135592
Nov. 30, 2009 (JP) ................................. 2009-271633

(51) Int. Cl.
| | | |
|---|---|---|
| A61K 39/02 | (2006.01) | |
| A61K 39/00 | (2006.01) | |
| A61K 49/00 | (2006.01) | |
| A61K 9/127 | (2006.01) | |
| A61K 39/39 | (2006.01) | |
| A61K 39/145 | (2006.01) | |
| A61K 39/12 | (2006.01) | |

(52) U.S. Cl.
CPC ............. *A61K 9/127* (2013.01); *A61K 9/1272* (2013.01); *A61K 39/0241* (2013.01); *A61K 39/12* (2013.01); *A61K 39/145* (2013.01); *A61K 39/39* (2013.01); *A61K 2039/55555* (2013.01); *A61K 2039/55594* (2013.01)

(58) Field of Classification Search
CPC .......... A31K 9/00; A31K 9/127; A31K 39/00; A31K 39/02; A31K 39/12
See application file for complete search history.

(56) References Cited

U.S. PATENT DOCUMENTS

| | | |
|---|---|---|
| 5,994,090 A | 11/1999 | Matsuda et al. |
| 2003/0008321 A1 | 1/2003 | Fukui et al. |
| 2003/0064079 A1 | 4/2003 | Goudie et al. |
| 2003/0147914 A1 | 8/2003 | Keich et al. |
| 2003/0224037 A1 | 12/2003 | Eriguchi et al. |
| 2008/0038329 A1 | 2/2008 | Uchida et al. |
| 2009/0263823 A1 | 10/2009 | Matsuda et al. |

FOREIGN PATENT DOCUMENTS

| | | |
|---|---|---|
| EP | 0 677 295 A1 | 10/1995 |
| EP | 0 767 176 A1 | 4/1997 |
| EP | 2 027 865 A1 | 2/2009 |
| EP | 2213735 A1 | 8/2010 |
| JP | 62-050665 A | 3/1987 |
| JP | 7-304789 A | 11/1995 |
| JP | 2009-007279 A | 1/2009 |
| WO | 99/52547 A1 | 10/1999 |
| WO | 00/16746 A2 | 3/2000 |
| WO | 00/23106 A1 | 4/2000 |
| WO | 01/34189 A2 | 5/2001 |
| WO | 02/49666 A2 | 6/2002 |
| WO | 02/098465 A2 | 12/2002 |
| WO | 03/003941 A2 | 1/2003 |
| WO | 2004/026336 A1 | 4/2004 |
| WO | 2007/006712 A2 | 1/2007 |

(Continued)

OTHER PUBLICATIONS

Rechnitzer, H. et al. Current Microbiology, vol. 53, pp. 293-297, 2006.*
Rechnitzer, H., et al. Current Microbiology, vol. 53, pp. 293-297, 2006.*
Notification of Transmittal of Translation of the International Preliminary Report on Patentability (Forms PCT/IB/326) of International Application No. PCT/JP2010/003732 mailed Jan. 26, 2013 with forms PCT/IB/373, PCT/IB/338 and PCT/ISA/237.
Extended European Search Report dated Jun. 20, 2013, issued in corresponding European Patent Application No. 10783165.3.

(Continued)

*Primary Examiner* — Rodney P Swartz
(74) *Attorney, Agent, or Firm* — Westerman, Hattori, Daniels & Adrian, LLP

(57) ABSTRACT

Disclosed is a vaccine which has a high therapeutic effect on *mycoplasma* infection and is highly safe. For the purpose of developing effective therapeutic methods for *mycoplasma* infection, *mycoplasma*-mimic particles which are effective as a vaccine for *mycoplasma* infection are provided, and also provided are bacterium-mimic particles including common bacteria. Bacterium-mimic particles such as *mycoplasma*-mimic particles can be provided by producing liposome particles in which a lipid antigen specific to a pathogenic bacterium such as *mycoplasma* is contained as a liposome-constituting lipid component. The administration of the *mycoplasma*-mimic particles enables the induction of a potent immunological activity in living bodies. The *mycoplasma*-mimic particles can be used as an excellent vaccine for the prevention or treatment of *mycoplasma* infection.

9 Claims, 21 Drawing Sheets

(56) References Cited

FOREIGN PATENT DOCUMENTS

WO 2007/145362 A1 12/2007

OTHER PUBLICATIONS

Rechnitzer, H. et al., "Reconstituted Proteolipid Vesicles Prepared from Mycoplasma fermentans Membranes Are Able to Bind and Fuse with Molt-3 Cells", Current Microbiology, vol. 53, No. 4, Aug. 28, 2006, p. 293-297; cited in Extended European Search Report dated Jun. 20, 2013.

Cirillo, V.P. et al., "Sealed Vesicles Prepared by Fusing Mycoplasma Gallisepticum Membranes and Preformed Lupid Vesicles", Israel Journal of Medical Sciences, vol. 23, No. 5, May 1, 1987. p. 380-383; cited in Extended European Search Report dated Jun. 20, 2013.

Brandenburg, K. et al., "Physicochemical characterization and biological activity of a glycoglycerolipd from Mycoplasma fermentans", European Journal of Biochemistry, vol. 270, No. 15, Aug. 1, 2003, p. 3271-3279; cited in Extended European Search Report dated Jun. 20, 2013.

Kawahito, Y. et al., "Mycoplasma fermentans glycolipid-aritigen as a pathogen of rheumatoid arthritis", Biochemical and Biophysical Research Communications, 369, 2008, pp. 561-566, Cited in TW Office Action dated Feb. 25, 2015.

Dascher, C.C. et al., "Immunization with a mycobacterial lipid vaccines improves pulmonary pathology in the guinea pig model of tuberculosis", International Immunology, 2003, pp. 915-925, vol. 15 cited in ISR.

Hiromatsu, K. et al., "Induction of CD1-restricted immune responses in guinea pigs by immunization with mycobacterial lipid antigens", Journal of Immunology, 2002, pp. 330-339, vol. 169 cited in ISR.

International Search Report of PCT/JP2010/003732, mailing date Aug. 3, 2010.

Haynes, "Influenza virus-like particle vaccines". Expert Reviews: Vaccines, 2009, pp. 435-445, 8(4).

Stanley, et al., "Immunobiology of Human Papillomavirus Infection and Vaccination-Imphcations for Second Generation Vaccines", Vaccine www.elsevier.com/locate/vaccine, (2008), pp. K62-K67.

Matsuda, et al., "Antigens: Lipids", Encyclopedia of Life Sciences, 2001, pp. 1-8.

Nishida, et al., "Synthesis and Absolute Configuration of a Novel Aminoglycoglycerolipid, Species-Specific Major Immunodeterminant of Mycoplasma fermentans", Tetrahedron Letters, 1999 (4 pages).

Nishida, et al. "Synthesis of Artificial Glycoconjugate Polymers Carriing 6-0-Phosphocholine a-D-Glucopyranoside, Biologically Active Segment of Main Cell Membrane Glycopids of Mycoplasma fermentans", J. Carbohydrate Chemistry, 1999, (12 pages).

Matsuda, et al. "Structure of a novel phosphocholine-containing aminoglycoglycerolipid of Mycoplasma fermeritans", Biochimica et Biophysica Acta, vol. 1349, 1997 (pp. 1-12).

Matsuda, et al. "Phosphocholine-Containing Glycoglycerolipids (GGPL-I and GGPL-III) Are Species-Specific Major Immunodeterminants of Mycoplasma fermentans", Biochemical and Biophysical Research Communications, vol. 233, article No. RC976443, 1997, (pp. 644-649).

Matsuda, et al., "Identification of Phosphocholine-Containing Glycoglycerolipids Purified from Mycoplasma fermentans-Infected Human Helper T-Cell Culture as Components of M. fermentans", Microbiology Immunology, vol. 39(5), 1995, (pp. 307-313).

Matsuda, et al. "Structure of a Novel Phosphocholine-containing Glycoglycerolipid from Mycoplasma fermentans". The Journal of Biological Chemistry, vol. 269, No. 52, issue of Dec. 30, 1994; (pp. 33123-33128).

Nishida, et al. "Synthesis and Absolute Configuration of 6-0-Phosphocholine-a-D-Glucopyransyl Glycerolipid Isolated From HTLV-I-Infected Cell Lines", Tetrahedron Letters, vol. 35, No. 30. 1994 (pp. 5465-5468).

Sato, et al. "Promotion of arthritis and allergy in mice by aminoglycoglycerophospholipid, a membrane antigen specific to Mycoplasma fermentans", FEMS Immunology Med Microbiology, vol. 59, 2010 (pp. 33-41).

Miyachi et al., "Synthesis and absolute structures of Mycoplasma pneumoniae β-glyceroglycolipid antigens" Carbohydrate Research 344 (2009) 36-43, Elservier Ltd., Japan, cited in Office Action issued in counterpart Japanese Patent Application No. 2011-518281 dated Mar. 25, 2015 (8 pages).

Kawahito et al., "Mycoplasma infectious disease and rheumatoid arthritis" Seitai No. Kagaku 59(5): 464-465, 2008, w/ English translation, cited in Office Action issued in counterpart Japanese Patent Application No. 2011-518281 dated Mar. 25, 2015 (7 pages).

T. Sugiyama, et al.; "Immunological Analysis of Glycolipids and Lipopolysaccharides Derived from Various Mycoplasmas"; Infection and Immunity, Dec. 1974, vol. 10, No. 6, pp. 1273-1279.

Marjatta Nurminen, et al.; "The Genus-Specific Antigen of Chlamydia: Resemblance to the Lipopolysaccharide of Enteric Bacteria"; National Public Health Institute, Jun. 17, 1983; pp. 1279-1281.

Jennifer M. Taylor, et al., "Helicobacter pylori lipopolysaccharide promotes a Th1 type immune response to immunized mice"; Vaccine 24 (2006), pp. 4987-4994.

Shosaku Motoda; "A complement-mediated immune lysis test using liposomes for the detection of antibodies to Mycoplasma pneumoniae"; Department of Virology; Apr. 21, 1986; vol. 41(5); pp. 757-765.

* cited by examiner

FIG. 4
(A)
| Size d.nm | Intensity % | Size d.nm | Intensity % |
|---|---|---|---|
| 0.4000 | 0.0 | 68.06 | 12.5 |
| 0.4632 | 0.0 | 78.82 | 16.0 |
| 0.5365 | 0.0 | 91.28 | 17.2 |
| 0.6213 | 0.0 | 105.7 | 16.0 |
| 0.7195 | 0.0 | 122.4 | 12.8 |
| 0.8332 | 0.0 | 141.8 | 8.6 |
| 0.9649 | 0.0 | 164.2 | 4.5 |
| 1.117 | 0.0 | 190.1 | 1.5 |
| 1.294 | 0.0 | 220.2 | 0.1 |
| 1.499 | 0.0 | 255.0 | 0.0 |
| 1.736 | 0.0 | 295.3 | 0.0 |
| 2.010 | 0.0 | 342.0 | 0.0 |
| 2.328 | 0.0 | 396.1 | 0.0 |
| 2.696 | 0.0 | 458.7 | 0.0 |
| 3.122 | 0.0 | 531.2 | 0.0 |
| 3.615 | 0.0 | 615.1 | 0.0 |
| 4.187 | 0.0 | 712.4 | 0.0 |
| 4.849 | 0.0 | 825.0 | 0.0 |
| 5.615 | 0.0 | 955.4 | 0.0 |
| 6.503 | 0.0 | 1106 | 0.0 |
| 7.531 | 0.0 | 1281 | 0.0 |
| 8.721 | 0.0 | 1484 | 0.0 |
| 10.10 | 0.0 | 1718 | 0.0 |
| 11.70 | 0.0 | 1990 | 0.0 |
| 13.54 | 0.0 | 2305 | 0.0 |
| 15.69 | 0.0 | 2669 | 0.0 |
| 18.17 | 0.0 | 3091 | 0.0 |
| 21.04 | 0.0 | 3580 | 0.0 |
| 24.36 | 0.0 | 4145 | 0.0 |
| 28.21 | 0.0 | 4801 | 0.0 |
| 32.67 | 0.0 | 5560 | 0.0 |
| 37.84 | 0.0 | 6439 | 0.0 |
| 43.82 | 0.2 | 7456 | 0.0 |
| 50.75 | 2.9 | 8635 | 0.0 |
| 58.77 | 7.6 | 1.000e4 | 0.0 |
(B)
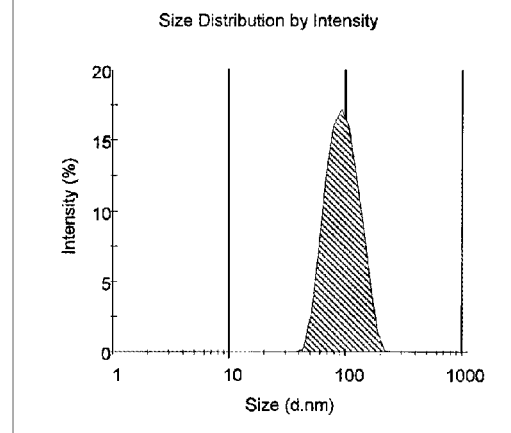
(C)
| Rec # | Z-Avg d.nm | Pk 1 Avg (I) d.nm | Pk 2 Avg (I) d.nm | Pk 3 Avg (I) d.nm | DCR kcps |
|---|---|---|---|---|---|
| 31 | 89.42 | 98.21 | 0.000 | 0.000 | 10528.6 |
FIG. 5
(A)
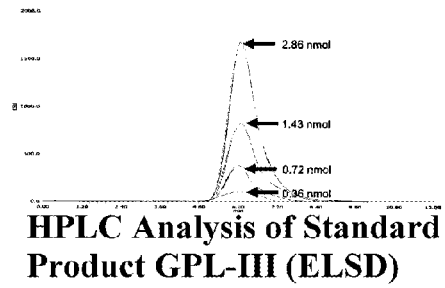
HPLC Analysis of Standard Product GPL-III (ELSD)
(B)
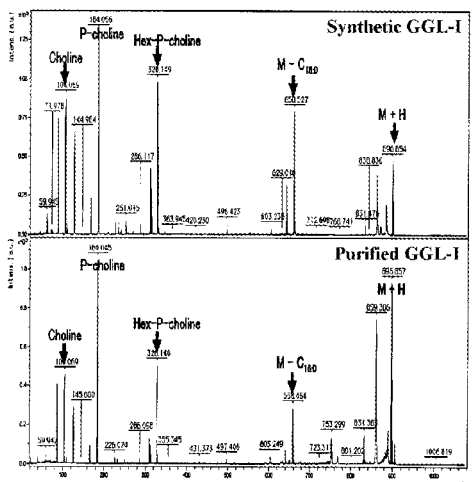
$y = 4E+07x - 5E+06$
$R^2 = 0.999$
Standard Curve of GGPL-III (ELSD)
(C)
MS/MS Analysis of GGL-I

FIG. 8
(A) IgG
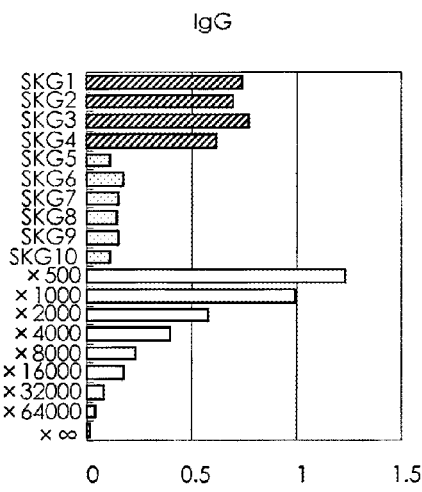
(B) IgM
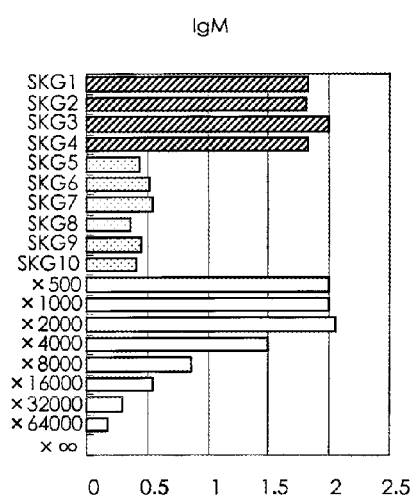
FIG. 9
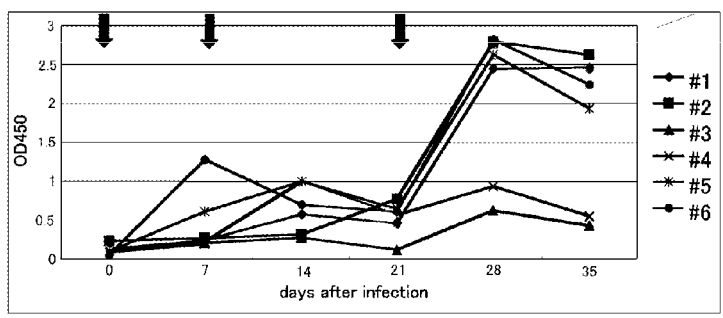

FIG. 10
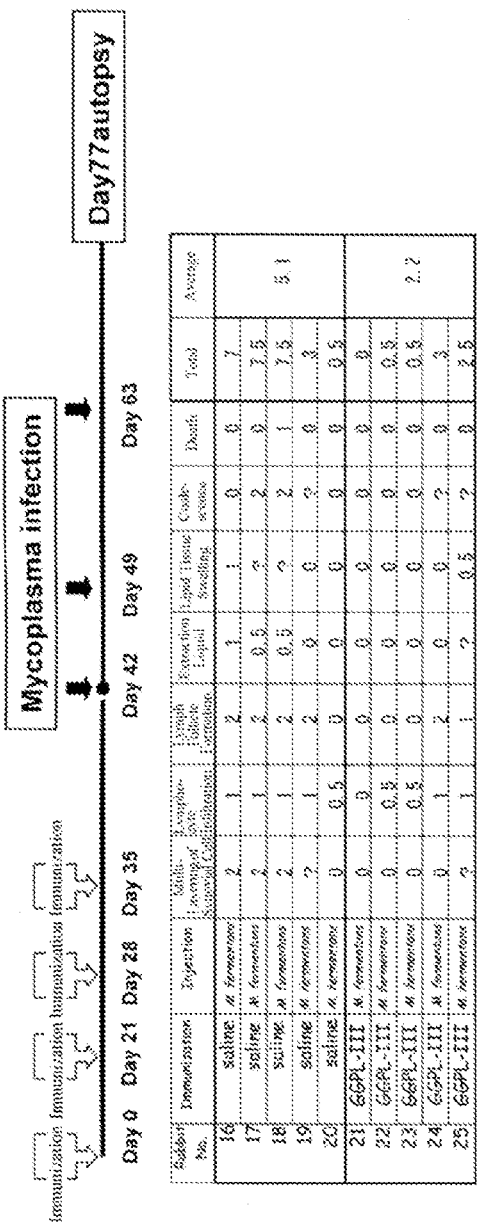
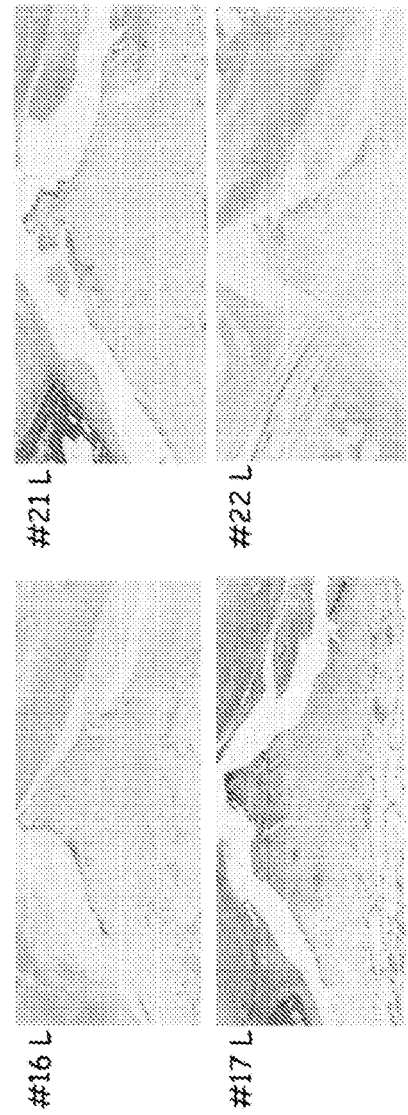

Adjuvant Effect of Lipid Antigen

Fig. 18
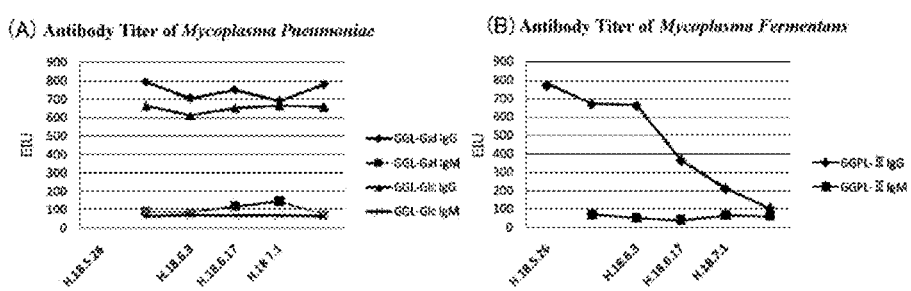
Fig. 19
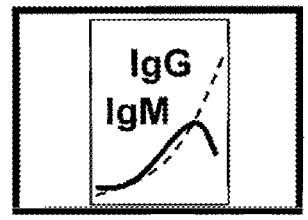
Expand of clinical symptons
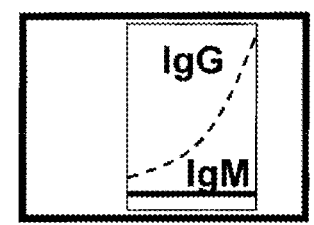
Increase of Mp GGL Gal-type IgG

FIG. 23

|   | GGPL-III(ug) | DPPC(ug)/Percent(%) | Cholesterol(ug)/Percent(%) | Average Particle Size(nm)/ Distribution Percent(%) |
|---|---|---|---|---|
| 1 | 300 | 189/90 | - | 61, 280/80:20 |
| 2 | 300 | 105/50 | - | 23, 300/79:21 |
| 3 | 300 | 42/20 | - | 17, 150, 2210/35:45:20 |
| 4 | 300 | 94/45 | 50/45 | 37, 288/39:61 |
| 5 | 300 | 2/25 | 28/25 | 23, 350/57:43 |
| 6 | 300 | 21/10 | 11/10 | 22, 100/42:58 |
| 7 | 300 | - | - | 12.9, 111, 345/23:39:33 |
| 8 | - | 210/100 | - | 84, 877, 5110/73:22:4 |
| 9 | - | 105/50 | 56/50 | 110, 4820/97:3 |

VACCINE FOR MYCOPLASMA INFECTION

TECHNICAL FIELD

The present invention relates to bacterium-mimic particles using a specific lipid antigen in bacteria for example *mycoplasma*, and a vaccine for *mycoplasma* infection using thereof, which has high therapeutic effects and is highly safe, and a prevention or treatment method for *mycoplasma* infection using the vaccine.

BACKGROUND ART

*Mycoplasma* is known to infect animals such as human, domestic animals, and pets, and to cause various diseases. Particularly, in human, *mycoplasma* is believed to be strongly associated with not only pneumonia, but also respiratory diseases caused by chronic or repetitive *mycoplasma* infection such as asthma and chronic obstructive pulmonary disease (COPD), rheumatic diseases such as rheumatoid arthritis (Non-patent Document 1), and neural diseases such as multiple sclerosis, and currently most potential candidate as a causative microorganism for these chronic diseases called intractable diseases (FIG. 1, and Non-patent Documents 31 and 32).

Cases of *Mycoplasma* infection that stemmed from cold symptoms such as fever, cough, and pneumonia, and developed into asthma, chronic obstructive pulmonary disease (COPD), multiple sclerosis, or a rheumatic disease are known. At the time, it is known that reactivation or exacerbation of the symptoms repeats and transfers gradually to a chronic disease, and thus along with early diagnosis and early treatment, prevention or treatment of exacerbation (gradual aggravation of the symptoms) or reactivation (aggravation of the symptoms again after the symptoms become less severe once) are especially important.

However, with a conventional examination method, it was difficult to grasp diagnosis of *mycoplasma* infection or progression of treatment for *mycoplasma* infection. Thus, details for the diagnosis of *mycoplasma* infection or the progression of treatment for *mycoplasma* infection are not clarified, and therefore, the present situation is that there are many patients who receive no appropriate prevention or treatment. A diagnosis method for *mycoplasma* infection that is most widely used currently is a serum diagnosis method. However, the conventional diagnosis method is an antibody assay method by culturing *Mycoplasma pneumoniae* in a large amount, and using a crude extract from a fungus body thereof, and thus has problems in specificity, detection sensitivity, and quantitative property, and has difficulty in early diagnosis of *mycoplasma* infection.

The present inventors focused attention on a lipid antigen on the surface of various bacteria belonging to a *mycoplasma* genus, and discovered multiple kinds of lipid antigens specific to respective bacterium from the past. The present inventors succeeded in separation, purification, and structure-determination of these specific lipid antigens, and also succeeded in chemical synthesis for some of the lipid antigens (Patent Documents 1 to 8).

Diagnostic products using these specific lipid antigens for *mycoplasma* infection have high specificity and sensitivity in comparison with existing diagnostic products, and lead to establishment of a quantitative measurement method for the change of the antibody titer, and it can be said that early diagnosis for *mycoplasma* infection, which has been a problem so far, can be tentatively resolved.

However, a therapeutic agent for *mycoplasma* infection that is in practical use as a therapeutic agent that can be currently most expected for the treating effects, is some antibiotics such as macrolide-based, or newquinolone-based, or tetracycline-based antibiotics, but such antibiotics have great adverse effects, and also have big problems such as advent of drug-resistant strains, which leads the *mycoplasma* infection to become severe while sufficient treating effects are not expected, and becomes a cause for transfer to a chronic disease.

On the other hand, a vaccine therapy for *mycoplasma* is not developed for human. The reasons therefor are that a live vaccine, an attenuated vaccine, and the like have problems in safety and are difficult to practically use, and a killed vaccine or the like has a problem of an allergic reaction by contamination of a horse serum in a culture fluid, and the like. In addition, an example of the reason is that identification of efficacious, specific antigen protein is not possible yet even with progress of peptide or DNA analysis in order to specify a specific antigen protein that leads to vaccine induction. As for a vaccine for domestic animals such as a pig or a cow, live vaccines, attenuated vaccines, or the like, conventionally used are under further improvements (Patent Documents 9 to 12). A vaccine using a protein antigen was also developed (Patent Documents 13 to 15). Recently, a vaccine that was targeted to an enzyme that was associated with tissue damage by *mycoplasma* infection, was developed (Patent Document 16). However, all of these vaccines only have effects of suppressing pneumonia, or effects of suppressing inflammation, and cannot be said to be a vaccine having small toxicity and being effective even as a vaccine for domestic animals.

As described above, an effective prevention or treatment method for *mycoplasma* infection was rarely found conventionally, and thus there is an urgent need for development of an effective preventive or therapeutic agent for *mycoplasma* infection, particularly, a vaccine for *mycoplasma* infection.

In the meantime, it is known that in production of a vaccine in various pathogenic virus, target's pathogenic virus-mimic particles are prepared, and immunization is conducted using the virus-mimic particles whereby to obtain high immune response. In addition, development of a vaccine preparation having high activity and high safety using the virus-mimic particles is also in progress (Non-patent Document 2). A vaccine incorporated into a liposome and the like in an antigen peptide of virus are also in a direction to practical use (Non-patent Document 3).

A virus self-duplicates a structure protein, an enzyme, and the like using a cell mechanism, coats a membrane of the cell, and goes out of the cell and grows. Consequently, a virus has no lipid antigen in a cell membrane, and most of vaccines are from a virus particle or a protein antigen. A virus has extremely small size, and also has small structural components on the surface, and thus it is relatively simple to imitate virus particles, i.e., provide virus-mimic particles that are mistaken as invasion of virus itself by the immune system of an organism.

On the other hand, bacteria including *mycoplasma* can self-duplicate by DNA, and produces basically unique structural components of a lipid membrane, and thus the membrane lipid component is specific to a respective bacterium, and complicated. Consequently, it is difficult to analyze structural components of a cell membrane or membrane lipids, and in further consideration of a wide variety of cell components, membrane proteins, and the like, it is difficult to conceive of mimicking *mycoplasma* itself simply with only one component among them, and thus the concept of

*mycoplasma*-mimic particles or bacterium-mimic particles was not familiar. Usually, it is unclear which component among these many components remains as essential, and how to provide *mycoplasma*-mimic particles using a particle preparation technique, and it is unclear whether such *mycoplasma*-mimic particles cause immune response enough for *mycoplasma* infection and mistaking of the biological immune system.

CITATION LIST

Patent Document

Patent Document 1: Japanese Patent No. 3735388
Patent Document 2: Japanese Patent No. 3551525
Patent Document 3: Japanese Patent No. 3717962
Patent Document 4: International Publication No. WO 2007/023583
Patent Document 5: Japanese Patent Application Laid-Open (JP-A) No. 2007-238470
Patent Document 6: International Publication No. WO 2007/145361
Patent Document 7: International Publication No. WO 2007/145362
Patent Document 8: JP-A No. 2009-7279
Patent Document 9: JP-A No. 2009-73855
Patent Document 10: Japanese Patent Application National Publication (Laid-Open) No. 2004-537543
Patent Document 11: Japanese Patent Application National Publication (Laid-Open) No. 2004-518655
Patent Document 12: Japanese Patent Application National Publication (Laid-Open) No. 2004-536106
Patent Document 13: JP-A No. 2006-311824
Patent Document 14: Japanese Patent Application National Publication (Laid-Open) No. 2005-515162
Patent Document 15: Japanese Patent Application National Publication (Laid-Open) No. 2003-513935
Patent Document 16: Japanese Patent Application National Publication (Laid-Open) No. 2009-500007
Patent Document 17: Japanese Patent Application National Publication (Laid-Open) No. 2006-503830
Patent Document 18: JP-A No. 2005-145959
Patent Document 19: Japanese Patent Application National Publication (Laid-Open) No. 2002-526436
Patent Document 20: International Publication WO 2002/098465 (WO 2002/098465)
Patent Document 21: JP-A No. 2008-37831
Patent Document 22: JP-A No. 2001-69977
Patent Document 23: JP-A No. 2002-241313
Patent Document 24: Japanese Patent No. 2828391
Patent Document 25: JP-A No. 2004-010481
Patent Document 26: Japanese Patent Application No. 2007-288728
Patent Document 27: Japanese Patent No. 2828391

Non-Patent Document

Non-patent Document 1:
Non-patent Document 2: Influenza virus-like particle vaccines. Haynes J R. Expert Rev Vaccines. 2009 April; 8 (4): 435-45. Review
Non-patent Document 3: Immunobiology of human papilloma virus infection and vaccination implications for second generation vaccines. Stanley M, Gissmann L, Nardelli-Haefliger D. Vaccine. 2008 Aug. 19; 26 Suppl 10: K62-7. Review.
Non-patent Document 4: Mol. Immunol. 25: 10, 1025-1031, 1988
Non-patent Document 5: Matsuda K, Saito M, Yamamoto N Encyclopedia of Life Science. Vol. 1 p 748-755, Nature publishing group, (2001)
Non-patent Document 6: M. Kraft, Q. &Hamid, J Allergy Clin Immunol 117, 1197-1198. (2006)
Non-patent Document 7: M. Kraft, G. H. Cassell, J. E. Henson, H. Watson, J. Williamson, B. P. Marmion, C. A. Gaydos, & R. J. Martin, Am J Respir Crit Care Med 158, 998-1001. (1998)
Non-patent Document 8: F. Meloni, E. Paschetto, P. Mangiarotti, M. Crepaldi, M. Morosini, A. Bulgheroni, &A. Fietta, J Chemother 16, 70-76. (2004)
Non-patent Document 9: J. Haier, M. Nasralla, A. R. Franco, & G. L. Nicolson, Rheumatology (Oxford) 38, 504-509. (1999)
Non-patent Document 10: H. W. Clark, M. R. Coker-Vann, J. S. Bailey, & T. M. Brown, Ann Allergy 60, 394-398. (1988)
Non-patent Document 11: E. Maida, J Neurol 229, 103-111. (1983)
Non-patent Document 12: G. L. Nicolson, M. Y. Nasralla, J. Haier, & J. Pomfret, J Clin Neurosci 9, 525-529. (2002)
Non-patent Document 13: F. Daxbock, K. Zedtwitz-Liebenstein, H. Burgmann, & W. Graninger, Ann Hematol 80, 180-182. (2001)
Non-patent Document 14: C. Leen, S. & Ling, Arch Dis Child 75, 266-267. (1996)
Non-patent Document 15: J. Nijs, G. L. Nicolson, P. De Becker, D. Coomans, & K. De Meirleir, FEMS Immunol Med Microbiol 34, 209-214. (2002)
Non-patent Document 16: G. K. Endresen, Rheumatol Int 23, 211-215. (2003)
Non-patent Document 17: MATSUDA Kazuhiro, TATANO-ARITOMI Keiko, IITA-TANAKA Naoko, SHINGU Yuko, TETSUO Tomiyama, HARASAWA Ryo, MORITA Oji, KUSUNOKI Susumu, The Japanese Society of Mycoplasmology No. 34, 45-46 (2007)
Non-patent Document 18: Matsuda, K., et al., The Japanese Society of Mycoplasmology, Magazine No. 31, 35-36 (2004)
Non-patent Document 19: Kazuhiro MATSUDA, The Japanese Society of Mycoplasmology, NO. 35, 41-43 (2008)
Non-patent Document 20: Miyachi, A., Miyazaki, A., Shingu, Y., Matsuda, K., Dohi, H., Nishida, Y., Carbohydrate Research 344: 36-43 (2009)
Non-patent Document 21: Nishida, Y., Takamori, Y., Ohrui, H., Ishizuka, I., Matsuda, K., Kobayashi, K., Tetrahedron lett. 40: 2371-2374 (1999)
Non-patent Document 22: Nishida, Y., Takamori, Y., Matsuda, K., Ohrui, H., Yamada, T., Kobayashi, K., J. Carbohydr. Chem. 18: 65-72 (1999)
Non-patent Document 23: Matsuda, K., Ishizuka, I., Kasama, T., Handa, S., Yamamoto, T., Biochim. Biophys. Acta 1349: 1-12 (1997)
Non-patent Document 24: Matsuda, K., Li, J-L., Harasawa, R., Yamamoto N. Biochem. Biophys. Res. Com. 233: 644-649 (1997)
Non-patent Document 25: Matsuda, K., Harasawa, R., Li, J. L., Kasama, T., Taki, T., Handa, S., Yamamoto, N., Microbiolo. Immunol. 39: 307-313 (1995)
Non-patent Document 26: Matsuda, K., Kasama, T., Ishizuka, I., Handa, S., Yamamoto, N., Taki, T. J. Biol. Chem. 269: 33123-33128 (1994)

Non-patent Document 27: Nishida, Y., Ohrui, H., Meguro, H., Ishizawa, M., Matsuda, K., Taki, T., Handa, S., Yamamoto, N., Tetrahedron Lett. 35: 5465-5468 (1994)

Non-patent Document 28: Ishida, N., Irikura, D., Matsuda, K., Sato, S., Sone, T., Tanaka, M., Asano, K, Molecular Cloning and Expression of a Novel Cholonephosphotransferase Involved in Glycerophospholipid Biosynthesus of *Mycoplasma fermentans*. Curr Microbiol (2009 in press)

Non-patent Document 29: Matsuda, K., Li, J-L., Harasawa, R., Yamamoto N. Phosphocholine-containing glycoglycerolipids (GGPL-I and GGPL-III) are species-specific major immunodeterminants of *Mycoplasma fermentans*. Biochem. Biophys. Res. Com. 233: 644-649 (1997)

Non-patent Document 30: C. Leen, S. & Ling, Arch Dis Child 75, 266-267. (1996)

Non-patent Document 31: Kawahito, Y., Ichinose, S., Sano, H., Tsubouchi, Y., Kohno, M., Yoswhikawa, T., Tokunaga, D., Hojo, T., Harawsawa, R., Nakano, T., Matsuda K. *Mycoplasma fermentans* glycolipid-antigen as a pathogen of rheumatoid arthritis. Biochem. Biophys. Res. Com. 369: 561-566 (2008)

Non-patent Document 32: M. F. Barile, *Mycoplasma* and leukemia, Ann N Y Acad Sci 143: 557-572 (1967) Non-patent Document 33: Sato, N., Oizumi, T., Kinbara, M., Funayama, H., Sato, S., Matsuda, K., Endo, Y. FEMS Immunology and Microbiology 59: 33-41 (2010)

SUMMARY OF THE INVENTION

Problems to be Solved by the Invention

An object of the present invention is to provide a vaccine that has high therapeutic effects for *mycoplasma* infection and is safe, and to develop an effective prevention or treatment method for *mycoplasma* infection. Another object of the present invention is to provide *mycoplasma*-mimic particles that are efficacious as a vaccine for *mycoplasma* infection, and further to provide bacterium-mimic particles, wherein said bacterium includes all of the commonly known bacteria.

Means for Solving the Problems

The present inventors separated and purified lipid antigens specific to each species of various pathogenic *mycoplasma* of human, pig, etc., and particularly for GGL Glc-type and GGL Gal-type, which are lipid antigens specific to human pathogenic *Mycoplasma pneumoniae*, and for GGPL-I and GGPL-III, which are lipid antigens specific to *Mycoplasma fermentans*, the present inventors determined respective structure, and then also succeeded in the chemical synthesis in the past (Patent Documents 1 to 8) (Non-patent Document 5). Then, the present inventors developed and established a diagnosis method that allows specific detection of antibody in the serum in high sensitivity using these specific lipid antigens, for *mycoplasma* infection. Furthermore, the present inventors focused attention on the fact that each of these lipid antigens is specific to each *mycoplasma* species, and continued researches earnestly with an aim to produce efficacious vaccine preparations using these lipid antigens.

In the meantime, researches and development for a carrier for a stable vaccine preparation were actively conducted conventionally. Furthermore, there are developments in progress of a vaccine composition in which an immunogen is coated on the surface of particles (Patent Document 17), and a technique that uses a liposome preparation as a preparation for diagnosis or for a vaccine, in which an antigen protein, various allergens, and the like are bonded to the membrane surface of the liposome via a hydrophobic peptide and the like, and a liposome as a carrier (Patent Document 18 to 20). In addition, there are also known examples showing that a liposome prepared using a phospholipid to which an antigen is bonded, has an action as a T cell activator (Patent Document 21). Conversely, in a case when an antigen is a phospholipid antigen, the phospholipid antigen is incorporated as a structural component of the liposome membrane, and used in an antibody detection method (complement-dependent liposome dissolution assay) using a property that the phospholipid antigen reacts with an antibody, whereby the liposome is destructed by complement action. However, the use is limited merely for antibody screening or diagnosis of the phospholipid antigen (Patent Document 22 and Non-patent Document 4).

However, the present inventors focused attention on the fact that *mycoplasma* has the least size among bacteria and has simple cell membrane structure nearly without a cell wall, and furthermore has a lipid membrane as a main component of a cell membrane. The present inventors came up with a stable, uniform preparation of liposome particles from purified specific lipid antigen. The liposome particles are thought to possibly cause the same immunity reaction to the *mycoplasma* infection as *mycoplasma*-mimic particles when subjected to an immune system of a living body.

Consequently, the present inventors purified chemical synthetic products of 2 kinds of each lipid antigen of *Mycoplasma pneumoniae* and *Mycoplasma fermentans*, and investigated various methods for shaping liposomes, and succeeded in preparation of stable liposome particles. In addition, the present inventors also separated and purified lipid antigens specific to *Mycoplasma hyorhinis* and *Mycoplasma hyopneumoniae*, which are causative for pig *mycoplasma* diseases, and then succeeded in preparation of liposome particles from them in the same method. Furthermore, on the basis of the analysis results of lipid structural components of the *mycoplasma* cell membrane, the present inventors prepared the simplest and functional particles that imitate a specific lipid antigen, and even also imitate the fatty acid composition of lipid components constituting the mimic particles.

Then, the present inventors immunized various model experiment animals using the *mycoplasma*-mimic particles prepared as described above, and thus could find out effects of the vaccine that can induce strong immune reactions for any particles. Particularly, *mycoplasma*-mimic particles which had lipid components as structural components of a *mycoplasma* cell membrane and were adjusted to have uniform particle sizes, had high immune induction activity.

The present inventors proceeded in analysis of the activities of *mycoplasma*-mimic particles, and as a result, found out that the *mycoplasma*-mimic particles were extremely simple structural components and well reflected immunological activities of *mycoplasma*, and were stable. Not only a lipid antigen, but also a fatty acid moiety such as phospholipid and cholesterol reflects more accurately immune response of a living body for *mycoplasma* by the structural components on the basis of the *mycoplasma* component analysis.

A conventional vaccine using a liposome is those obtained by binding a protein, a peptide, a carbohydrate and the like to a lipid constituting a liposome, or by putting forth a protein, a peptide, a carbohydrate and the like into the liposome. However, in the lipid antigen bacterium-mimic particles of the present invention, a lipid antigen itself is a structural component of a liposome, and thus the lipid antigen bacterium-mimic particles of the present invention are all extremely simplified particles, and are stable and have small toxicity and high safety.

In addition, it could be found out that the present bacterium-mimic particles exhibited actions and effects as an adjuvant (Non-patent Document 33). In addition, it could be found out that the immune induction activity on the basis of the specific lipid antigen of the present invention induced not only IgG and IgM, but also mucosal IgA, which strongly suggested possible use of the specific lipid antigen of the present invention as an adjuvant for mucosal immunity.

Then, the present inventors also applied the search method for the *mycoplasma*-specific lipid antigen to various other pathogenic bacteria than *mycoplasma*, and found out existence of a lipid antigen specific to each bacterium. With use of these specific lipid antigens, it is possible to prepare bacterium-mimic particles that induce activity specific to each species of bacteria. Furthermore, due to the fact that these bacteria are different in the fatty acid composition of each of the cell membrane-constituting lipid components, it is possible to produce bacterium-mimic particles, and a vaccine using the same for each bacterium by setting most suitable composition and particle size of a liposome in each bacterium by applying the optimization method in *mycoplasma* in accordance with analysis results for lipid components in each bacterium.

The present inventors have completed the present invention with obtaining the finding described above.

Specifically, the present invention is as described below.

(1) Bacterium-mimic particles, containing: liposome particles including one or more kinds of lipid antigens specific to a pathogenic bacterium as a liposome-constituting lipid component.

(2) *Mycoplasma*-mimic particles, containing: liposome particles including one or more kinds of *mycoplasma*-specific lipid antigens as a liposome-constituting lipid component.

(3) The *mycoplasma*-mimic particles according to (2) described above, wherein at least one kind of the *mycoplasma*-specific lipid antigen is a *mycoplasma*-specific glycolipid that is extracted, and then separated and purified from a preparation of a *mycoplasma* fungus body.

(4) The *mycoplasma*-mimic particles according to (2) described above, wherein at least one kind of the *mycoplasma*-specific lipid antigen is a specific glycolipid that is chemically or enzymatically synthesized, and then separated and purified.

(5) The *mycoplasma*-mimic particles according to any one of (2) to (4), wherein at least one kind of the *mycoplasma*-specific lipid antigen is a *Mycoplasma pneumoniae*-specific lipid antigen, or a *Mycoplasma fermentans*-specific lipid antigen.

(6) The *mycoplasma*-mimic particles according to any one of (2) to (5) described above, further containing: phosphatidyl choline, phosphoglycerol, and/or cholesterol as the liposome-constituting lipid component.

(7) The *mycoplasma*-mimic particles according to any one of (2) to (6) described above, wherein the liposome-constituting lipid components containing the *mycoplasma*-specific lipid antigen are mixed in a solvent, and then prepared as particles under conditions in which the particle diameter becomes in a range of 30 to 300 nm, and 80% or more thereof becomes in a range of 40 to 200 nm by ultrasonic wave treatment.

(8) The *mycoplasma*-mimic particles according to any one of (2) to (7) described above, which are *mycoplasma*-mimic particles having other antigenic substances on the surfaces of the liposome particles, wherein the antigenecity of the other antigenic substance increases by adjuvant effects of the *mycoplasma*-specific lipid antigen.

(9) The *mycoplasma*-mimic particles according to (8) described above, wherein the other antigenic substance is a virus-derived antigen peptide.

(10) A vaccine for prevention or treatment of *mycoplasma* infection, containing the *mycoplasma*-mimic particles according to any one of (2) to (7) described above as an active ingredient.

(11) The vaccine for prevention or treatment of *mycoplasma* infection according to (10) described above, wherein the *mycoplasma* infection is pneumonia, asthma, or a rheumatic disease.

(12) A method of preventing or treating a *mycoplasma* infection, containing: a process of administering the vaccine for prevention or treatment of *mycoplasma* infection according to (10) or (11) described above at least once to human or an animal that is affected or suspected to be affected with the *mycoplasma* infection.

(13) The method of treating *mycoplasma* infection according to (12) described above, containing: in the method of treating *mycoplasma* infection using the vaccine; a process of measuring the amount of a *mycoplasma* species-specific lipid antigen or the amount of a lipid antigen-specific antibody before and/or after administration of the vaccine, and a process of determining administration time and dosage amount of the next vaccine based on the measured value.

(14) A vaccine for prevention or treatment of a virus infection disease, containing: the *mycoplasma*-mimic particles according to (9) described above containing a virus-derived antigen peptide on the surface of the particles as an active ingredient.

(15) The vaccine according to (14) described above, wherein the virus is influenza virus and the virus infection disease is influenza.

(16) A method of preventing or treating a virus infection disease, containing: a process of administering the vaccine for prevention or treatment of a virus infection disease according to (14) or (15) described above to human or an animal that is affected or suspected to be affected with the virus infection disease.

(17) The prevention or treatment method according to (16) described above, wherein the virus is influenza virus and the virus infection disease is influenza.

The present invention is bacterium-mimic particles which are characterized by containing liposome particles including a lipid antigen specific to a pathogenic bacterium as a liposome-constituting lipid component.

Effects of the Invention

The bacterium-mimic particles such as *mycoplasma*-mimic particles of the present invention can provide a stable liposome preparation having a uniform particle diameter. These bacterium-mimic particles can effectively induce strong humoral and cellular immunities by being administered to mammalian animals such as a human or a pig, and also have high IgA induction activity that is mucosal immunity, and thus can be used not only for a vaccine preparation for *mycoplasma* infection, but also as an adjuvant for a vaccine for virus or other pathogenic microorganism infection, or as an adjuvant for IgA induction. Then, these vaccine preparations and adjuvant preparations can provide a safe and stable preparation having no toxicity, and thus are extremely useful. In addition, particularly with respect to the adjuvant for IgA induction, there was only an adjuvant having high toxicity such as metal aluminum, as an adjuvant having high efficacy conventionally, and thus the bacterium-mimic particles such as *mycoplasma*-mimic particles of the present invention are extremely revolutionary.

Particularly, in human *mycoplasma* infection, a diagnosis method for *Mycoplasma fermentans* and *Mycoplasma pneumoniae*, which are causative for the human *mycoplasma* infection, was already established by previous researches of the present inventors. From this, it is possible to establish a system for diagnosis, prevention, and treatment on the basis of pathological molecular mechanism of the *mycoplasma* infection by providing the vaccine preparation according to the present invention.

BRIEF DESCRIPTION OF THE DRAWINGS

FIG. 4(a) represents the size and intensity of lipid antigens specific to *Mycoplasma hyorhinis* and *Mycoplasma hyopneumoniae*. The particle diameter was measured with an apparatus for measurement of the Zeta potential. FIG. 4(b) represents the size distribution by intensity of lipid antigens specific to *Mycoplasma hyorhinis* and *Mycoplasma hyopneumoniae*. FIG. 4(c) shows the quality control of the liposome particle size is measurement values of the liposome particle size in accordance with Zetasizer.

FIG. 5(a) represents a quantitation analysis (HPLC Analysis) of purified *Mycoplasma fermentans*-derived antigenic lipids GGPL-I and GGPL-III. FIG. 5(b) represents a quantitation analysis (Standard curve) of purified *Mycoplasma fermentans*-derived antigenic lipids GGPL-I and GGPL-III. FIG. 5(c) represents a quantitation analysis (MS/MS Analysis) of purified *Mycoplasma fermentans*-derived antigenic lipids GGPL-I and GGPL-III.

FIG. 8(a) represents induction of IgG antibody by interperitoneal immunity of SKG-blood mouse (autoimmune disease model) using the *Mycoplasma fermentans*-mimic particles (synthesis GGPL-III). FIG. 8(b) represents induction of IgM antibody by interperitoneal immunity of SKG-blood mouse (autoimmune disease model) using the *Mycoplasma fermentans*-mimic particles (synthesis GGPL-III).

FIG. 9 represents preparation of an animal model using a viable bacterium of *Mycoplasma fermentans*. Through administration experiments to rabbits of the transtracheal model and the trans-knee articular model, increase of the blood IgG antibody titer (vaccine activity) was observed.

FIG. 10 represents immunity function-priming effects of a synthetic lipid antigen in an animal model using the *Mycoplasma fermentans*-mimic particles. For a rabbit of *Mycoplasma fermentans* infection rheumatoid arthritis model, joint lesion could be suppressed by interperitoneal multiple immunizations of the *Mycoplasma fermentans*-mimic particles.

FIGS. 11(A) to (E) show the distribution of *Mycoplasma fermentans* specific lipid antigen (GGPL-III) in the synovial tissue derived from rheumatoid arthritis patient. FIGS. 11(A) and 11(B) show the immunohistochemical staining of tissues into which a number of mononuclear cells have been invaded. The arrow heads in FIG. 11(A) show the representative positively stained mononuclear cells. Anti GGPL-III antibody was used as a primary antibody. FIG. 11(B) is the negative control of FIG. 11(A, wherein anti-mouse IgM antibody was used as a primary antibody. FIG. 11(D) is the negative control of FIG. 11(C), wherein anti-mouse IgM antibody was used as a primary antibody. FIG. 11(E) represents immunoelectron microscopic observation of tissue containing synovial cells. Anti-GGPL-III antibody was used as a primary antibody. Anti-IgG and anti-IgM antibodies attached with gold colloidal particles were used as secondary antibodies. The arrow heads show signals derived from the gold colloidal particles.

FIG. 14(A) shows that administration of *Mycoplasma fermentans*-mimic particles (GGPL-III) along with metal nickel (antigen) to the ears of a mouse had effects of enhancing antibody producibility dose-dependently (administrations of 0.2 mg/ml and 1 mg/ml). FIG. 14(B) shows that the *Mycoplasma fermentans*-mimic particles (GGPL-III) have equivalent cell immunity activity to that of LPS.

FIG. 15(A) represents the approximate curve by standard serum, and FIG. 15(B) represents the EIU value of each serum.

It was found out that the production amount of interferon γ increased by 2 folds or more when *mycoplasma*-mimic particles (GGPL-I, GGPL-III) were added as compared with administration of interleukin 2 alone using human peripheral-blood mononuclear cells. The mononuclear cells were separated from the peripheral blood of a healthy individual, and a sample in which interleukin 2 and the lipid antigen were added to the mononuclear cells, and a sample of the mononuclear cells without adding the lipid antigen were cultured, and supernatants thereof were recovered, and the amounts of interferon γ in the supernatants were measured with an enzyme antibody immune method (ELISA method).

FIG. 17(A) represents results of antibody titer measurements (ELISA method) of *Mycoplasma pneumoniae* in a patient of juvenile rheumatoid arthritis. FIG. 17(B) represents results of antibody titer measurements (ELISA method) of *Mycoplasma fermentans* in a patient of juvenile rheumatoid arthritis.

FIG. 18(A) represents results of antibody titer measurements (ELISA method) of *Mycoplasma pneumoniae* in a patient of sarcoidosis. FIG. 18(B) represents results of antibody titer measurements (ELISA method) of *Mycoplasma fermentans* in a patient of sarcoidosis.

FIG. 19 represents the variation of the serum antibody in a patient of multiple sclerosis.

Figure 20:
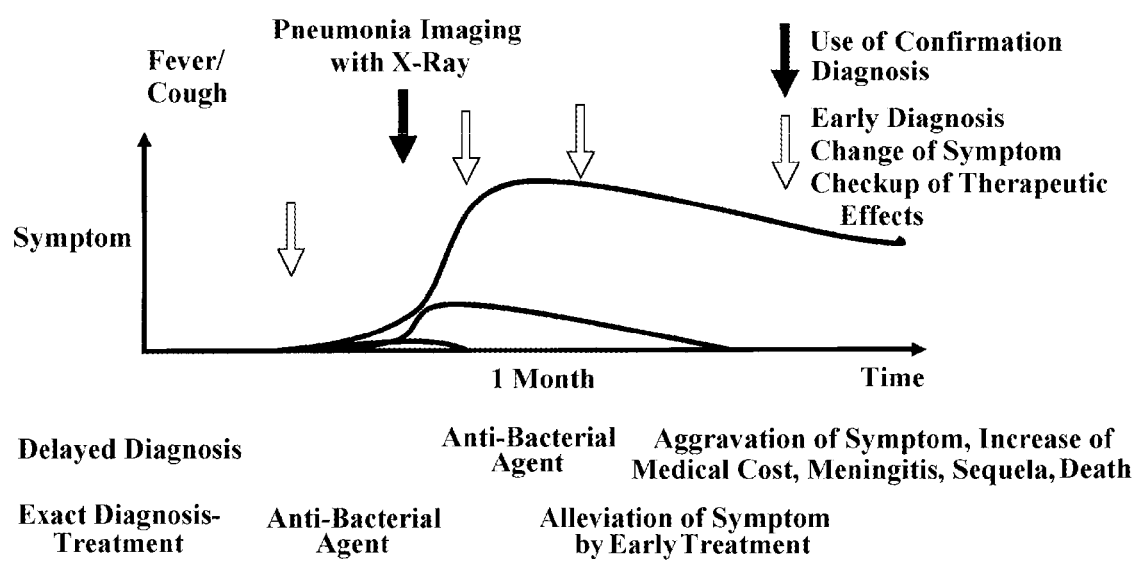

FIG. 20 represents a protocol of diagnosis, prevention, and treatment for juvenile pneumonia *mycoplasma*.

Figure 21:
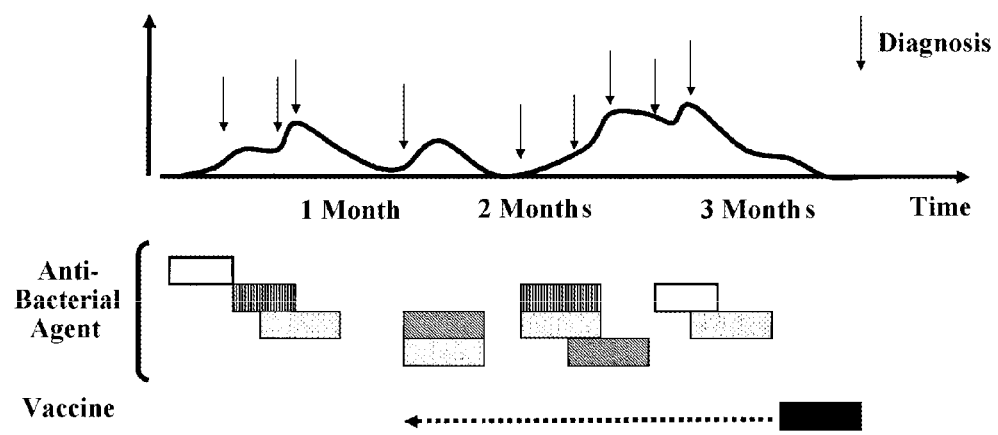

FIG. 21 represents a protocol of diagnosis, prevention, and treatment for adult pneumonia *mycoplasma*.

Figure 22:
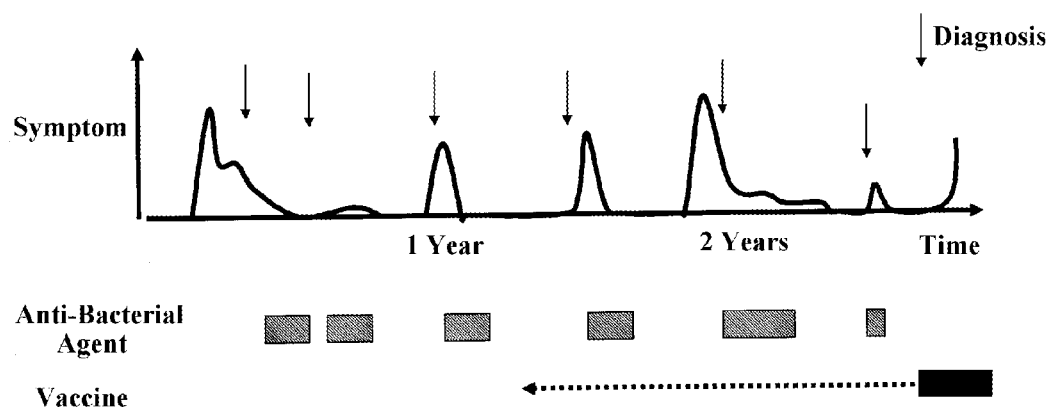

FIG. 22 represents a protocol of diagnosis, prevention, and treatment for chronic *mycoplasma* infections such as autoimmune diseases.

FIG. 23 represents investigation of the composition of the *mycoplasma*-mimic liposome particles.

Figure 24:
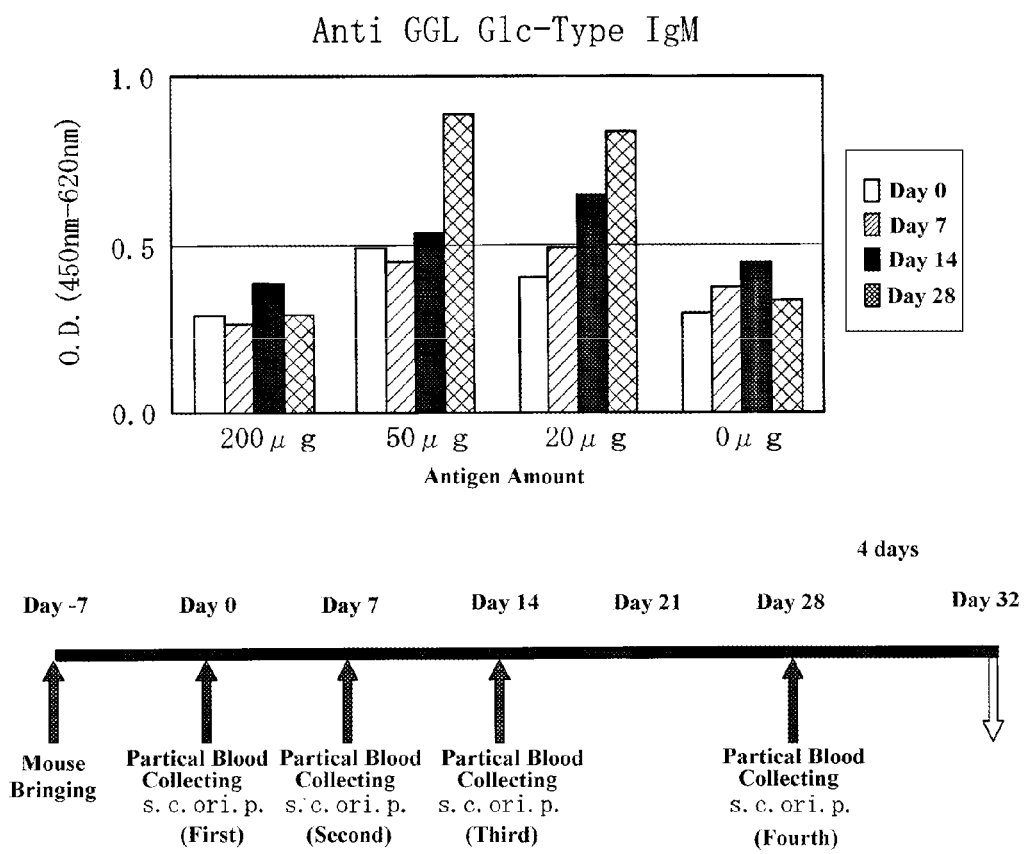

FIG. 24 represents optimization of administration method for the *mycoplasma*-mimic liposome particles.

Figure 25:
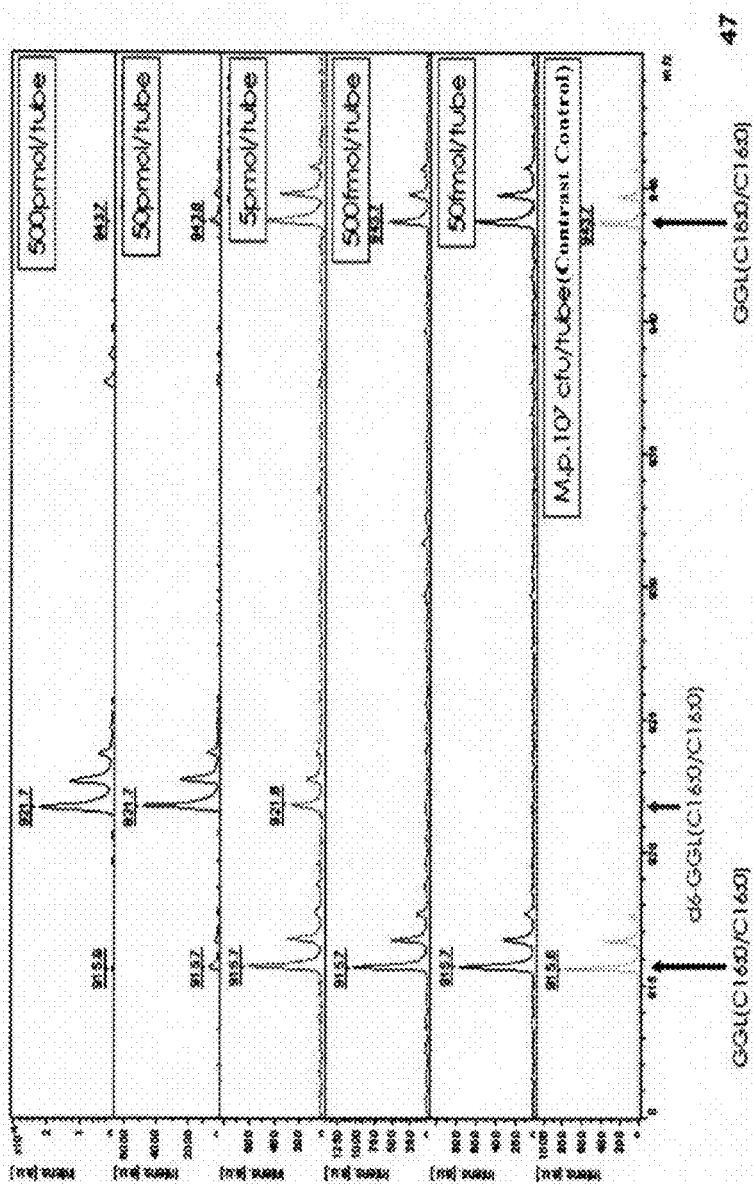

FIG. 25 represents quantitation of a *mycoplasma*-specific lipid antigen (GGL) (mass analysis method)

Figure 26:
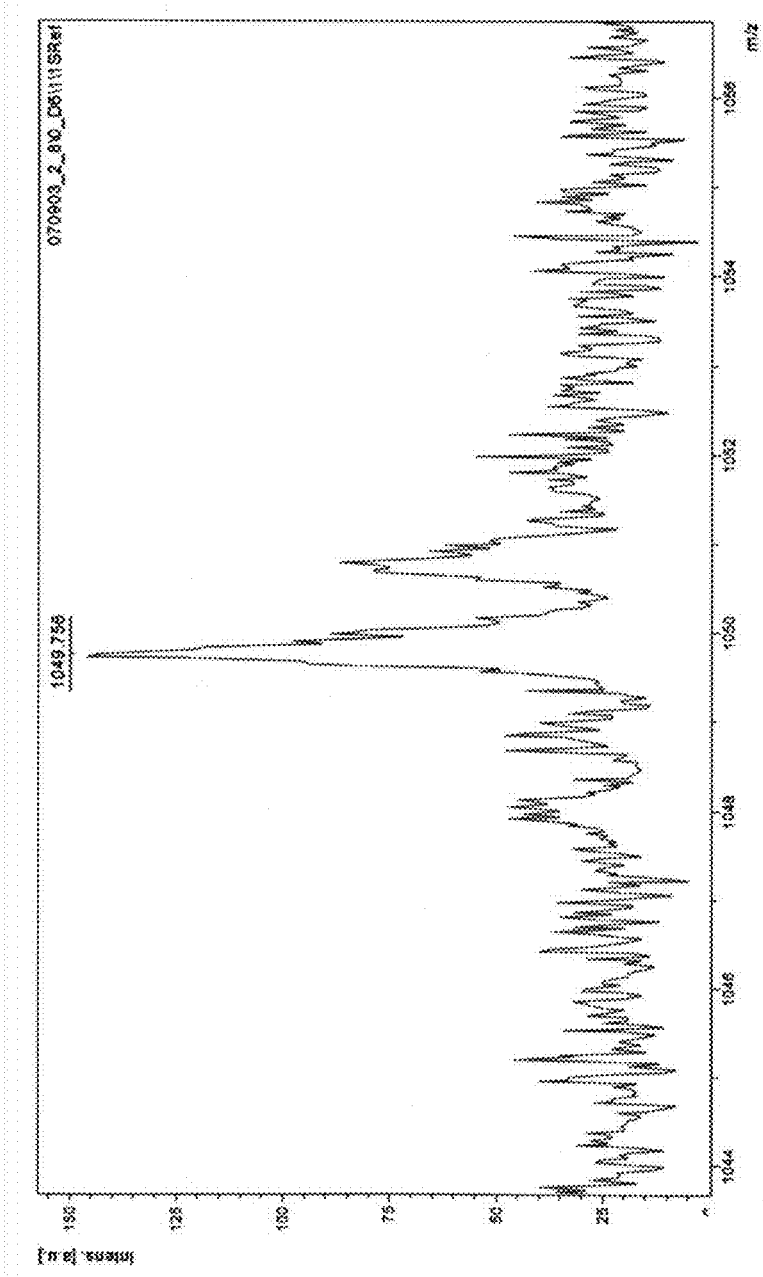

FIG. 26 represents detection of *Mycoplasma fermentans*-specific lipid antigen GGPL-III that is deposited on the articular tissue in a patient of rheumatoid arthritis (by a mass analysis apparatus).

Figure 27:
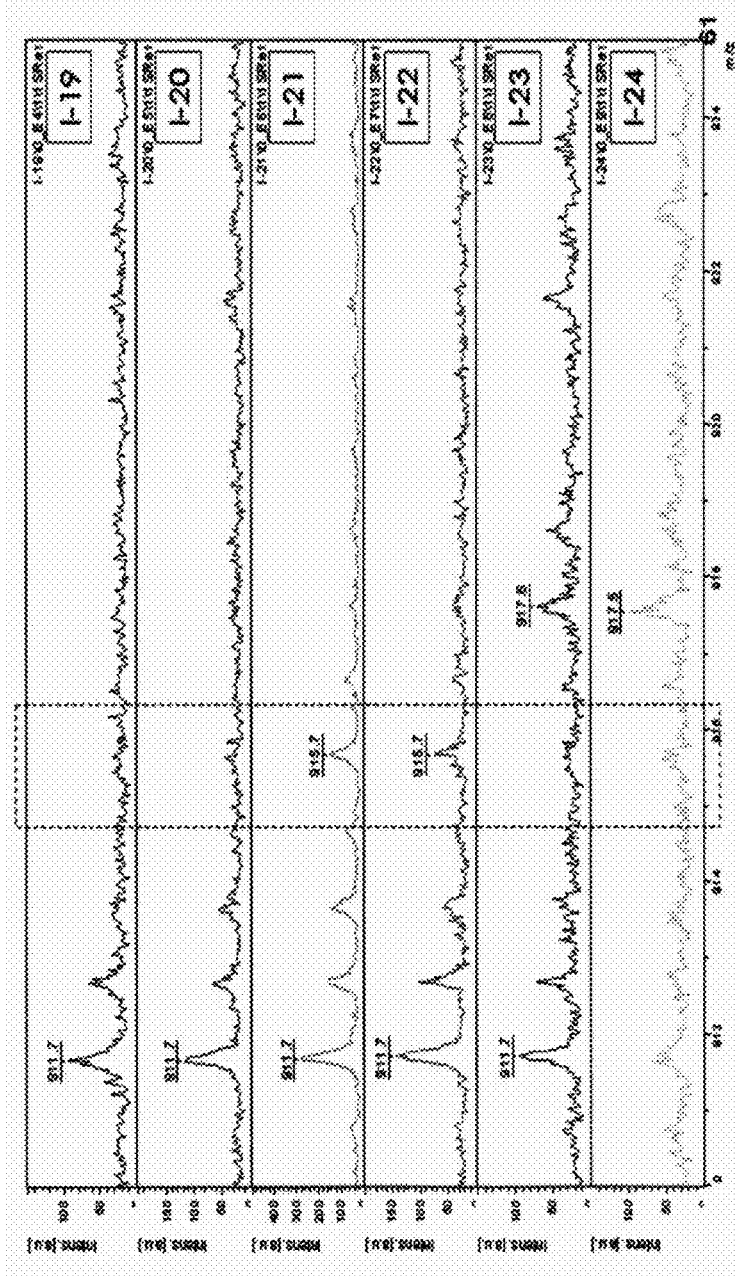

FIG. 27 represents identification of the peaks of the *Mycoplasma pneumoniae*-specific lipid antigen from the pharyngeal swab liquid of a subject patient.

MODES FOR CARRYING OUT THE INVENTION

1. Regarding *mycoplasma* Infection

*Mycoplasma* infects animals such as human, domestic animals, and pets, and various diseases are known. Particularly, in human, it is understood out that *mycoplasma* is causative not only for pneumonia, but also for respiratory diseases such as asthma (Non-patent Documents 6 and 7) and chronic obstructive pulmonary disease (COPD) (Non-patent Document 8), rheumatic diseases such as rheumatoid arthritis (Non-patent Documents 9 and 10), neural diseases such as multiple sclerosis (Non-patent Document 11), amyotrophic lateral sclerosis (ALS) (Non-patent Document 12) and Guillain-Barre syndrome, blood diseases such as hemolytic anemia (Non-patent Document 13), allergic diseases such as atopic dermatitis, cardiovascular diseases such as arteriitis, arterial sclerosis, and Kawasaki disease (Non-patent Document 14), psychiatric diseases such as chronic fatigue syndrome (CFS) (Non-patent Document 15) and fibromyalgia syndrome (FMS) (Non-patent Document 16), Gulf War illnesses, etc.

Figure 1:
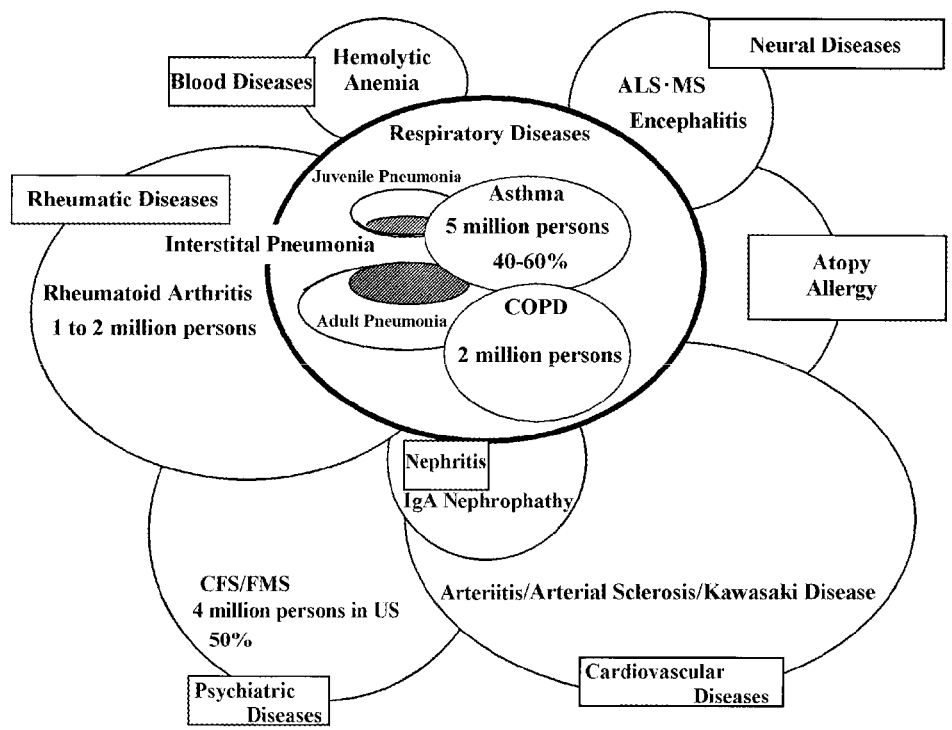
FIG. 1 is a conceptual diagram of the relationship between a *mycoplasma* infection and a disease.

*Mycoplasma* infection is said to be a most potential candidate as a cause for chronic intractable diseases such as asthma, chronic obstructive pulmonary disease (COPD), multiple sclerosis, and rheumatic disease. However, a diagnosis method and a therapeutic method having specific and quantitative properties that can follow progression of a chronic disease are not established, and thus relationship with the pathology is not sufficiently elucidated, and appropriate treatment is not carried out (FIG. 1).

Figure 2:
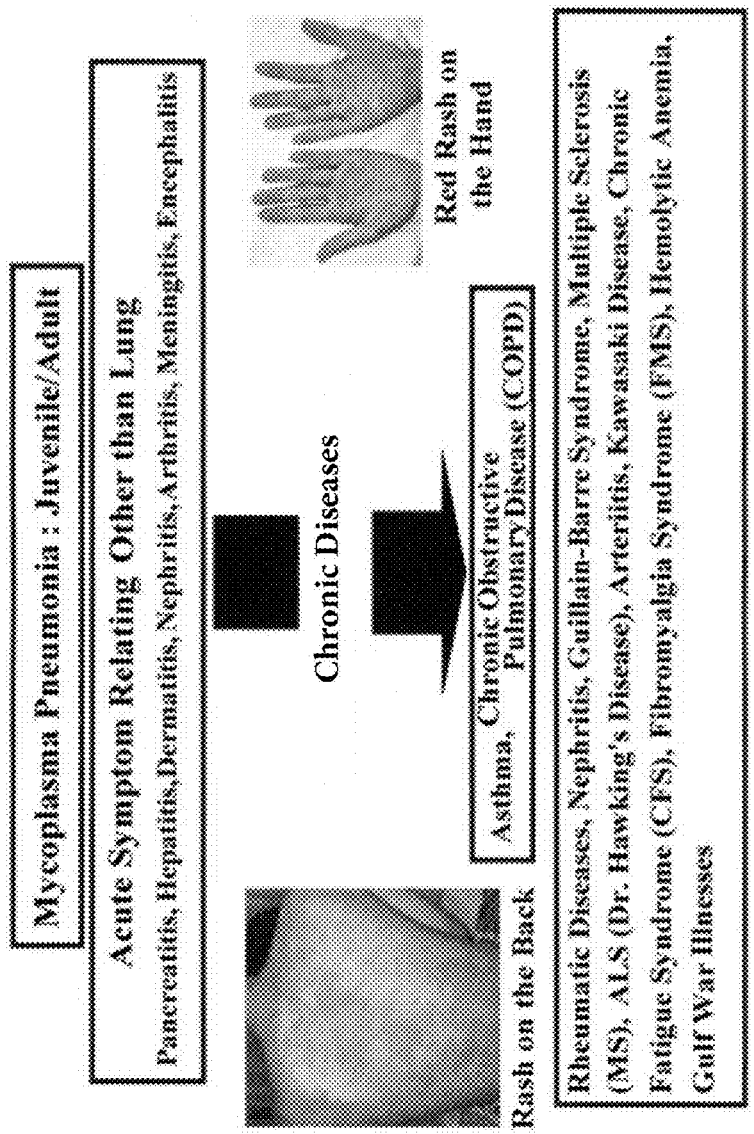
FIG. 2 represents acute symptoms of a *mycoplasma* infection and the development to chronic diseases.
Figure 3:
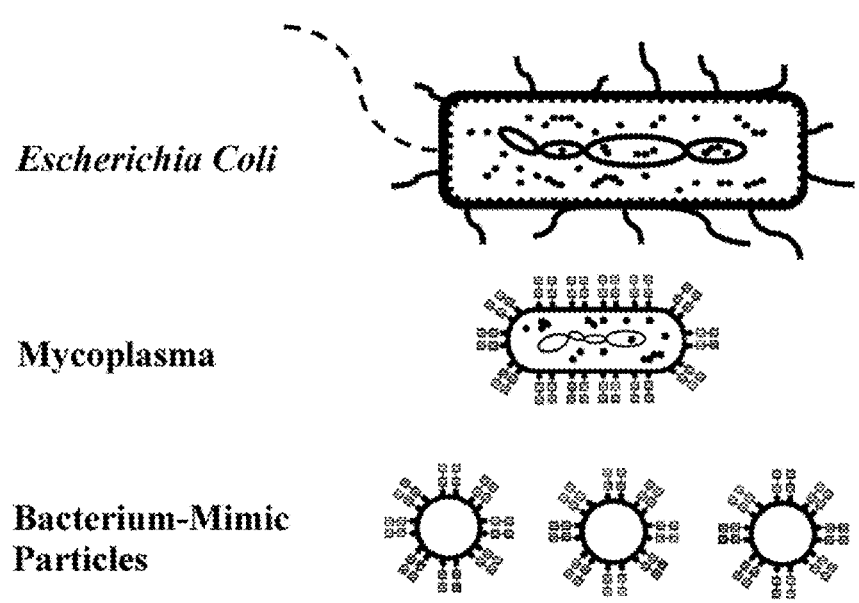
FIG. 3 is a conceptual diagram of the bacterium-mimic particles (*mycoplasma*-mimic particles).

*Mycoplasma* infection develops from cold symptoms such as fever, cough, and pneumonia, and there are cases of transfer to asthma, chronic obstructive pulmonary disease (COPD), multiple sclerosis, and a rheumatic disease (Non-patent Documents 17 and 18). At the time, it is known that reactivation or exacerbation of the symptoms repeats and transfers gradually to a chronic disease. However, with a conventional examination method, it was difficult to diagnose *mycoplasma* infection and grasp progression of the treatment. Thus, the present situations are that details are not clarified, and therefore, there are many patients who received no appropriate treatment (Non-patent Document 19) (FIG. 2).

It is known that *mycoplasma* infection to domestic animals such as a pig and a cow also causes a serious disease. For example, *Mycoplasma hyorhinis* and *Mycoplasma hyopneumoniae* are one of the causative bacteria for pig's respiratory infection, and *Mycoplasma bovis* is one of the causes for cow's respiratory infection.

2. Regarding *mycoplasma*-Specific Antigenic Lipid (2-1) Kind of Pathogenic *Mycoplasma*-Specific Lipid Antigen

*Mycoplasma pneumoniae* and *Mycoplasma fermentans* are currently known as human pathogenic *mycoplasma*. The present inventors separated and purified by two kinds of each of the *mycoplasma*-specific lipid antigens, determined the structures, and then chemically synthesized the *mycoplasma*-specific lipid antigens (Patent Documents 1 to 8 and Non-patent Documents 20 to 27). Specifically, for *Mycoplasma pneumoniae*, there are 2 kinds of GGL Glc-type and GGL Gal-type, and for *Mycoplasma fermentans*, there are 2 kinds of GGPL-I and GGPL-III.

Figure 13:
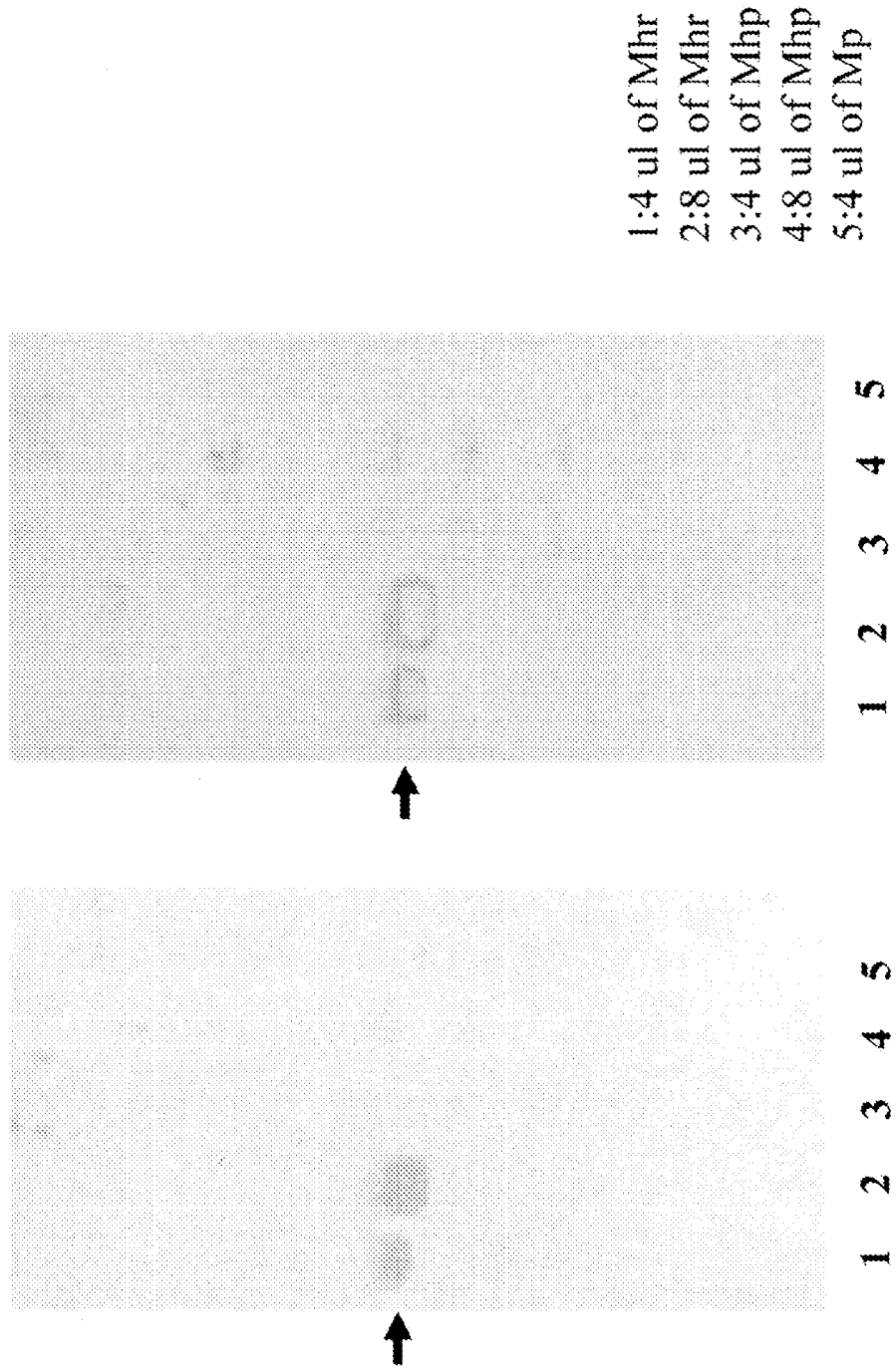
FIG. 13 represents detection of a lipid antigen specific to animal-derived *mycoplasma* (*Mycoplasma hyorhinis* and *Mycoplasma hyopneumoniae*).

In addition, it is known that *mycoplasma* infection to domestic animals such as a pig and a cow also causes a serious disease. For example, for a pig, there are respiratory infections such as pig's *mycoplasma* pneumonia, which are caused by *Mycoplasma hyorhinis* and *Mycoplasma hyopneumoniae*, and for a cow, there are cow's respiratory infections such as cow's *mycoplasma* pneumonia and diseases such as *mycoplasma* breast inflammation, which are caused by *Mycoplasma bovis*. At this time, each of the lipid antigens specific to *Mycoplasma hyorhinis* and *Mycoplasma hyopneumoniae* was separated and purified and prepared as liposome particles (FIG. 4). An experiment for immune activity evaluation was conducted for the obtained *mycoplasma*-mimic particles, whereby to confirm immune activity effects (FIG. 13).

(2-2) Production Method for *Mycoplasma*-Specific Lipid Antigen

The *mycoplasma*-specific lipid antigen in the present invention may be a *mycoplasma*-specific lipid antigen that is separated and purified from a membrane of target *mycoplasma*. When the chemical structural formula of the lipid is known (GGPL-I, GGPL-III, GGL Glc-type, GGL Gal-type, and the like), the *mycoplasma*-specific lipid antigen in the present invention that may be used, is preferably a lipid compound that is structure-determined by the method below (2-3), chemically synthesized, and purified (Patent Document 1 to 8). In addition, for example, a lipogenic enzyme specific to target *mycoplasma* is specified, and the enzyme itself may be used, or genes of the enzyme are cloned and, using a transformed cell, the specific lipid antigen may be obtained as a synthetic enzyme product in a large amount (Non-patent Document 28).

Hereinafter, a production method for GGPL-III, which is a typical *Mycoplasma fermentans*-specific lipid antigen, by extraction, separation and purification, and structure-determination, and the like, will be described in details. These methods may be adapted not only to other *mycoplasma*-specific lipid antigens, but also to a microorganism of extraction, separation and purification, and structure-determination of a lipid antigen-specific other pathogenic bacteria such as *chlamydia, rickettsia, tuberculosis bacterium, pneumococcus*, and the like.

(2-3) Separation, Purification, and Structure-Determination for *Mycoplasma*-Specific Lipid Antigen Hereinafter, an example of *Mycoplasma fermentans*-derived specific lipid antigen (GGPL-III) will be explained as a typical example (by a method of Patent Document 3, etc.).

(1) Separation and Purification of Glycolipid

Culture of *mycoplasma* at a PPLO medium was carried out as described below. *Mycoplasma* was cultured at 37° C. in a liquid medium in which 10% bovine serum, 10% penicillin, 0.0002% phenol red, and 1% glucose were added to PPLO liquid base medium (manufactured by Difco). Growth of the microorganism was confirmed with pH change of the medium, and then the medium was centrifuged at 16,000×g for 1 hour. This procedure was repeated once again to prepare a sample for lipid extraction. For 200 L (wet volume) of the microorganism sample, the lipid fraction was extracted with a mixed solvent of chloroform and methanol.

(2) Extraction of Lipid (GGPL-III)

The sample was floated in methanol for 4 hours to settle. A double amount of chloroform was added thereto, and the fungus body was crushed with ultrasonic wave, and further allowed to stand for 4 hours. The fungus body was centrifuged at 3000 rpm, and the supernatant was recovered and concentrated, to prepare a sample of the lipid fraction.

This lipid sample was separated and purified by a column chromatography filled with silica gel using chloroform and methanol. The lipid sample was developed with thin layer chromatography (TLC), stained with an orcinol reagent, and purified to obtain the target glycolipid fraction.

(3) NMR Analysis

The obtained lipid fraction was dissolved in a solution of DMSO-d6:$D_2O$=98:2, and $^1$H-NMR was measured at 60° C. Data of DQF-COSY spectrum attribution measured in 100% DMSO-d6 was obtained.

(4) Mass Analysis

For the obtained lipid fraction, analysis by ESI-MS measurement was performed.

(5) Structure-Determination and Chemical Synthesis

On the basis of the data obtained in (3) and (4) described above, structure-determination of glycolipid was tentatively performed, and respective skeleton was synthesized stereoselectively and regioselectively by chemical synthesis to determine the structure.

(6) Determination of Structure by Comparison of Data with Those of Chemical Synthetic Products For the obtained chemical synthetic products, 1H-NMR measurement was performed under the conditions of DMSO-d6:$D_2O$=98:2 at 60° C., which were similar to those for a natural product, and the spectrum thereof were analyzed and compared. As a result, the spectrum of the synthetic product was consistent with those of the natural product, whereby to determine the absolute structure.

(2-4) Enzyme Synthesis (by Method of Non-Patent Document 28)

A database of a target *mycoplasma* is searched, and lipogenic enzymes are synthesized in a large amount from transformed *Escherichia coli* using genes of candidate lipogenic enzymes, and a target-specific lipogenic enzyme is specified. An enzyme synthesis product may be obtained using the synthesis enzyme itself, or enzyme synthesis may be performed in a transformed cell that is transformed using the synthesis enzyme gene, whereby to obtain a specific lipid antigen in the medium in a large amount.

3. Regarding Target Bacteria of the Bacterium-Mimic Particles in the Present Invention When the "*mycoplasma*-mimic particles" is mentioned in the present specification, it refers to liposome particles that are obtained by purifying a lipid antigen specific to each species of *mycoplasma* and preparing liposome particles from the purified lipid antigen alone, or from a mixed lipid of the purified lipid antigen with another lipid such as phospholipid and cholesterol, wherein the liposome particles can cause immune response in the immune system in an organism which is susceptible of being infected with the *mycoplasma*.

Similarly, the "bacterium-mimic particles" refers to liposome particles that are obtained by purifying a lipid antigen specific to each species of pathogenic bacteria and preparing liposome particles from the purified lipid antigen alone, or from a mixed lipid of the purified lipid antigen with another lipid such as phospholipid and cholesterol, wherein the bacterium-mimic particles can cause immune response in the immune system in an organism which is susceptible of being infected with the pathogenic bacterium species.

The bacterium used in the bacterium-mimic particles of the present invention is typically *mycoplasma* that is used in the embodiments, but is not limited to *mycoplasma*, and may be bacteria having an antigenic lipid specific to the cell surface, and bacterium-mimic particles can be similarly produced by separating and purifying the specific antigenic lipid, and presenting the specific antigenic lipid to the liposome surface. Among these bacteria, *rickettsia* such as *Legionella, Chlamydia*, or the like, which is similar to *mycoplasma* in the size and the cell surface structure, is particularly suitable. The specific antigenic lipid may be chemically synthesized if it can be separated and purified and structure-determined, or may be enzyme-synthesized by cloning genes of the antigenic lipogenic enzyme.

Figure 6:
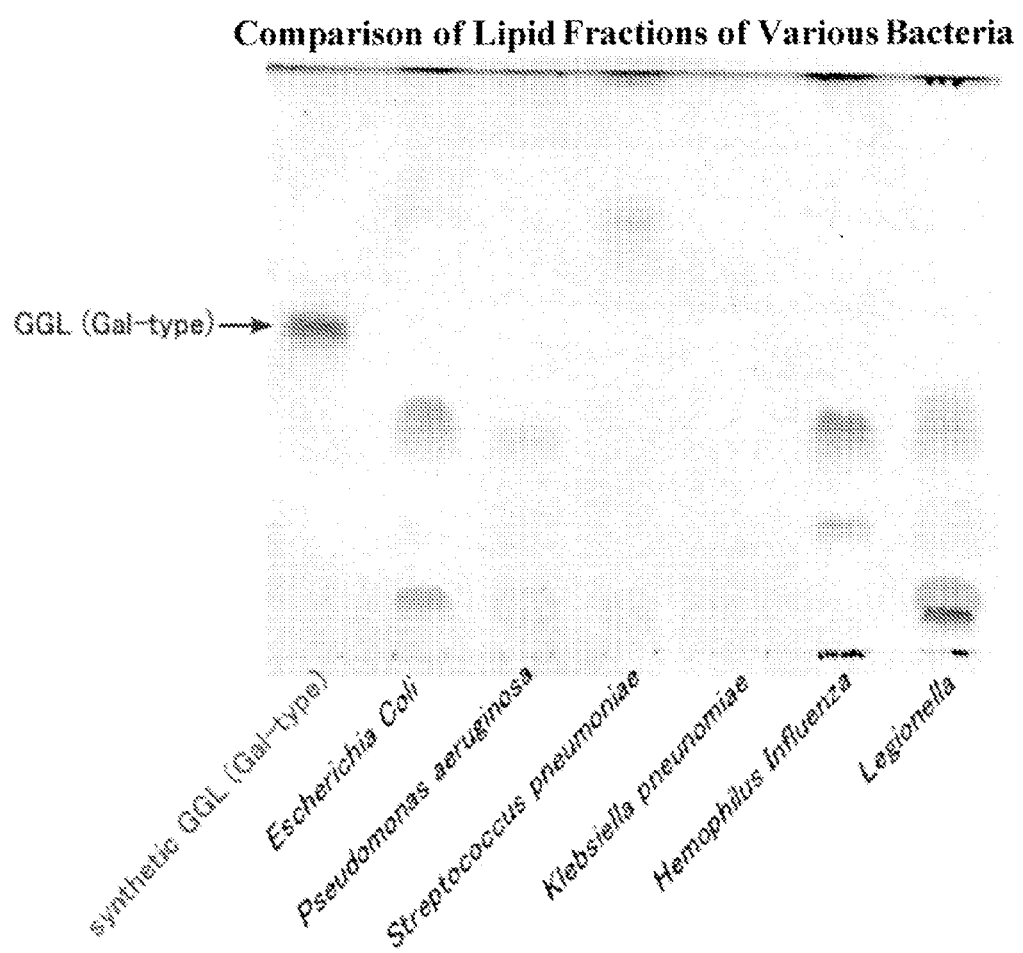
FIG. 6 represents comparison of lipid fractions of various bacteria, wherein there found are existences of specific lipids in *Escherichia coli, Pseudomonas aeruginosa, Pneumococcus, Klebsiella pneumoniae, Hemophilus influenzae* and *Legionella*.

This method may be adapted to other pathogenic bacteria such as *Helicobacter pylori* bacterium, *chlamydia, rickettsia, tuberculosis bacterium*, and *pneumococcus*, and the similar lipid antigen particles may be prepared and used. In FIG. 6, lipid fractions of various bacteria were compared, and specific lipids were admitted in respective bacterium of *Escherichia coli, Pseudomonas aeruginosa, pneumococcus, Klebsiella pneumoniae*, influenza *bacillus* and, *Legionella* bacterium. Specifically, respective bacterium was cultured in a large amount and fractionated with chloroform-methanol, and developed with a thin layer chromatography. After the development, the lipid fractions were stained with orcinol sulfuric acid and detected.

In addition, it becomes definite that specific lipid antigen also exists in *Helicobacter pylori* bacterium, and purified specific lipid antigen was obtained by applying the separation and purification method as described above for *mycoplasma*, and *Helicobacter pylori*-mimic particles were prepared in the same method as in the preparation method for the *mycoplasma*-mimic particles. Then, it could be found out that the *Helicobacter pylori*-mimic particles had induction activity of interferon γ in bone marrow cells of a C57BL/6 mouse (Example 13 and FIG. 12). This proves that the findings relating to the *mycoplasma*-mimic particles of the present invention may also be applied to other bacteria such as *Helicobacter pylori* and the like.

4. Preparation Method for Bacterium-Mimic Liposome Particles (4-1) Regarding Liposome The "liposome" is a micro-vesicle of a phospholipid double layer including water phase inside, and is formed by hydrating a lipid with a sufficient amount of water at a temperature of equal to or higher than the phase transition temperature. The liposome is classified into a multiple membrane liposome (MLV) containing multiple lipid double layers, and a single membrane liposome containing a single lipid double layer, when classified on the basis of the number of the lipid double layers. The latter is further classified on the basis of the size into small single membrane liposome (SUV), big single membrane liposome (LUV, REV) and macro-liposome (GUV). However, when the liposome or liposome particles are mentioned in the present specification, they refer to small single membrane liposome (SUV) containing a single lipid double layer, having hundreds or shorter nm of the diameter. The most suitable particle diameter of the liposome in the present specification varies on the target bacterium, but is in a range of tens to hundreds nm, and is preferably a uniform particle diameter as far as possible. For example, in *mycoplasma*, the particle diameter of the liposome is most preferably in a range of about 40 to 200 nm.

The phospholipid that constitutes the liposome is a main structural component of a biological membrane, and thus has low toxicity, and can be controlled for the particle size in accordance with administration purpose and administration method. Furthermore, the phospholipid has advantages that it can introduce antigen, antibody, sugar chain, and the like to a liposome by introducing a functional group into the surface of liposome particles, and can be targeted for a target site (target-orientated). Using these advantages, pharmaceutical researches are widely carried out (Patent Documents 23 to 26). These methods are techniques that can be used when the bacterium-mimic particles that are prepared as liposome particles in the present invention, are used as an adjuvant.

(4-2) Analysis Method for Lipid Antigen-Containing Liposome Particles (FIG. 5)

In order to administer the bacterium-mimic particles such as the *mycoplasma*-mimic particles of the present invention as a vaccine, it is necessary to provide the bacterium-mimic particles in constant stable quality in the particle size and the composition. Therefore, measurement of the particle size of the liposome particles, and establishment for analysis method for the composition are important.

HPLC is used in performing the composition analysis of the liposome particles in the present specification. A detector used in this analysis by HPLC is not particularly limited, and an ultraviolet absorbance detector, an evaporative light scattering detector (Hereinafter, it may be referred to as ELSD), or the like may be used. Among them, the evaporation light scattering detector (ELSD) is desirably used from a point that it can detect non-volatile components such as a lipid in high sensitivity, and allows high accurate quantitation.

When the composition analysis of the liposome is performed using HPLC, components in the liposome exhibit unique retention times (time period when a sample remains in a column), depending on the kind of a column to be used, the kind of a solvent to be used, and the flow rate. From this, it is possible to check the composition of each component. Each component eluted by HPLC can be quantitated. Particularly, with use of ELSD, or HPLC having a mass analysis device as a detector, liposome components can be analyzed for the composition in high sensitivity, high accuracy, and simplicity, and further exact quantitation can be carried out at the same time (FIG. 5). Accordingly, analysis by HPLC can be carried out in quality control in actual production process, whereby to secure stable quality.

(4-3) Method of Preparing a Liposome from the Specific Lipid Antigen of the Present Invention Many methods for preparation of a liposome itself are known [D. W. Deeamer, P. S. Uster, "Liposome" ed. by M. J. Ostro, Marcel Dekker Inc., N. Y. Basel, 1983, p 27]. A vortex method and an ultrasonic wave method are general, and in addition, an ethanol injection method, an ether method, a reverse phase evaporation method, and the like may be adopted, which are used in combination.

For example, in the vortex method and the ultrasonic wave method, a prescribed lipid is dissolved in an organic solvent, such as, methanol, ethanol, chloroform, or a mixture thereof, for example, a mixture of methanol and chloroform, and then the organic solvent is evaporated and removed, whereby to obtain a lipid thin layer. Then, this lipid thin layer is dissolved in an aqueous medium and subjected to vortex treatment or ultrasonic wave treatment, whereby to form a liposome. At this time, desired antigen or immunogen that is an active component such as a vaccine and the like may be mixed together, for example, dissolved or suspended in the aqueous medium described above, whereby to entrap the antigen or immunogen in the liposome.

When the lipid antigen is dissolved in an organic solvent, a synthetic lipid antigen may be dissolved in the organic solvent as described above along with the liposome-constituting lipid in the liposome production process, and then a liposome may be formed according to an ordinary method. The amount of the lipid antigen with respect to the amount of the liposome varies on the kind of the lipid antigen, the kind of other antigens than the target lipid antigen to be entrapped, the combination structure of the liposome, and the like, but generally 5 μg to 500 μg with respect to 1 mg of the other lipids constituting the liposome.

Among these liposome preparation methods, the preparation method for the liposome for the bacterium-mimic particles such as the *mycoplasma*-mimic particles of the present invention is preferably the ultrasonic wave method. Furthermore, the present inventors discovered that further uniform and highly stable liposome particles can be produced by combination of the ethanol injection method, which is first applied, and the ultrasonic wave method. In addition, by filtration with a filter having desired pore size, it is possible to order the particle size, and provide liposome particles having constant particle size and stable high quality.

(4-4) Optimization of the Lipid Antigen-Containing Liposome Particles of the Present Invention The *mycoplasma*-specific lipid antigen can form liposome particles alone. Thus, *mycoplasma*-mimic particles formed only with the *mycoplasma*-specific lipid antigen as a lipid component of the liposome particles are expected to cause strong immune response and exert sufficient vaccine activity when administered to a living body immediately after the particle preparation. However, the *mycoplasma*-mimic particles have various particle sizes, and are unstable, and thus are inadequate as a vaccine or an adjuvant, or an immune modulator or a diagnosis preparation. Consequently, when the *mycoplasma*-mimic particles are used as a vaccine preparation and the like, it is necessary to stabilize the synthetic lipid antigen, achieve more natural effects, and optimize safety by change of the constitution ratio of the liposome-constituting lipid or the size of the liposome. An optimal form of the liposome depends on effects to be expected for the liposome, and herein the effects mean effects as Drug Delivery System (DDS) or effects of antigen presentation, effects of antibody induction, effects as an adjuvant, and the like.

On the basis of basic data of physicochemical analysis of the *mycoplasma*-specific lipid antigen, optimal treatment conditions were investigated. As a result, it was found out that when the particle diameter is approximately 100 nm, the particle is most stable, allowing long time storage, and the optimal effects of the preparation as a stable preparation. That is to say, when the optimization of the optimal liposome preparation particles is mentioned in the *mycoplasma*-mimic particles, it refers that the *mycoplasma*-mimic particles make up a particle diameter in a range of 30 to 300 nm, and at the same time, and preferably meet the condition that 80% of the total particles is in a range of 40 to 200 nm.

In addition, in the liposome composition, cholesterol, which is essential in growth of *mycoplasma*, or a phospholipid such as phosphatidyl choline, which is a basic structural component, is used (FIG. 23). The most fatty acid has a length of the carbon number of 16 as a saturated type, and the next has a length of the carbon number of 18, and the next has a length of the carbon number of 14 in natural *Mycoplasma*. Thus, in accordance to this, results obtained using a synthesis antigen of the carbon number of 16 are shown. If particles are prepared only with a synthetic lipid antigen, the particle size or the distribution is not uniform, and thus the particle system and the distribution were measured with further change of the ratio of cholesterol to phosphatidyl choline of a saturated type having the carbon number of 16. From these results, it was found out that the molar ratio is preferably 10-50% lipid antigen, 20-50% phosphatidyl choline, and 10-50% cholesterol. This result was close to the analysis data of the *mycoplasma* lipid (Non-patent Document 29).

Consequently, when the optimization is mentioned in the *mycoplasma*-mimic particles, it refers that the liposome composition thereof is set such that the blending ratio of lipid antigen:phosphatidyl choline:cholesterol is in a range of 10 to 50:20 to 50:10 to 50 in molar ratio. Then, the carbon number of phosphatidyl choline, which is used at the same time, is 14 to 18, preferably 16, and the phosphatidyl choline is optimally phosphatidyl choline of a saturated type.

It was found out in the identification or purification process of the *mycoplasma* lipid antigen that structural components of the membrane lipid was not complicated, and was constituted mainly of phosphatidyl choline, cholesterol, and lipid antigens, and that the composition in the fatty acid portion is also extremely simple, and the like. In consideration of these results, stable and effective *mycoplasma*-mimic particles were prepared.

5. Characteristics of the Bacterium-Mimic Particles of the Present Invention

Actual *mycoplasma* infection causes bacteriolysis, incorporation into a cell, (lipid) antigen presentation, production of antibody, and immunity reactions of cells such as T cells or NKT cells. The similar reactions to the above can be induced by the *mycoplasma*-mimic synthetic liposome particles having the *mycoplasma*-specific lipid antigen.

In addition, for these bacterium-mimic liposome particles, structural components or size can be changed to be optimized depending on target functions.

Particularly, use of a purified synthetic lipid antigen renders the bacterium-mimic liposome particles to become a preparation having extremely specific immune activation ability, wherein said specific immune activation is completely free from the influence of *mycoplasma* components other than said lipid antigen. The bacterium-mimic liposome particles with the optimized length of the fatty acid and the like are further preferable. Since the structural components are simple, the bacterium-mimic liposome particles can be optimized to prepare a preparation in accordance with respective use such as antibody induction, a vaccine, an adjuvant, and a cell immunity therapy. For specific vaccine effects of a synthetic lipid antigen, the activity can be investigated using purified and synthetic lipid antigens, and using multiple *mycoplasma* species and multiple synthetic products of lipid antigens.

As the preparation method for the liposome, components that are close to the structural components on the basis of synthesized lipid antigen and *mycoplasma* lipid analysis were mainly investigated. With a liposome prepared with the structural components mainly composed of specific lipid antigens of respective bacterium, it was possible to prepare immune particles having characteristics of respective bacterium. By means of a method of accurately evaluating effects of the preparation such as increase of synthetic lipid antigens or antibody, it became possible to investigate and practically use the preparation. The bacterium-mimic particles of the present invention have an immune activity extremely close to that of *mycoplasma*, and further have no pathogenic recurrence in a live vaccine, etc., or impurity or lot difference in an inactivated vaccine, and has low toxicity.

6. Evaluation Method for Immune Activity of Synthetic Lipid Antigen Particles (6-1) Quantitation of Antibody Induction Activity by Interperitoneal Administration of Lipid Antigen Particles

*Mycoplasma* lipid antigen particles are interperitoneally administered 4 times to C57BL/6J mouse (8 weeks old female) interperitoneally. Partial blood collecting is performed right before the administration each time from the first to the third of the antigen administrations. After a lapse of 4 days from the fourth antigen administration, partial blood collecting (serum) is performed. Measurement of antibody is performed with ELISA coated with a specific lipid antigen. Secondary antibodies allow measurements of IgM and IgG. Furthermore, using a secondary antibody with respect to IgA, production of IgA, i.e., mucosal immune induction activity can be measured. Using the measurement results as a marker, optimizations of the amount, the composition, the shape, the solvent, and the like of the lipid antigens may be performed.

(6-2) Quantitation of Antibody Induction Activity by Intranasal Administration of Lipid Antigen Particles

*Mycoplasma* lipid antigen particles are interperitoneally administered 4 times to C57BL/6J mouse (8 weeks old female) interperitoneally. Partial blood collecting is performed right before the administration each time from the first to the third of the antigen administrations. After a lapse of 4 days from the fourth antigen administration, partial blood collecting (serum) is performed. Measurement of antibody is performed with ELISA coated with a specific lipid antigen. Secondary antibodies allow measurements of IgM and IgG. Furthermore, using a secondary antibody with respect to IgA, production of IgA, i.e., mucosal immune induction activity can be measured. Using the measurement results as a marker, optimizations of the amount, the composition, the shape, the solvent, and the like of the lipid antigens may be performed.

(6-3) Evaluation Method for Antibody Induction by Lipid Antigen Particles in Human It is found out that antibody assay and monitoring of antibody fluctuation in the serum of a *mycoplasma*-infected patient are possible (FIGS. 17 and 18), and this method can be adapted as it is. In addition, inhibition activity for *mycoplasma* growth can be measured with collected bloods.

(6-4) Detection and Quantitation of Lipid Antigens by Mass Spectrum A species-specific glycolipid antigen itself of *mycoplasma* can be detected and quantitated using the detection method for a lipid antigen using a mass spectrometer (mass analyzer) developed by the present inventors (Patent Document 6). Specifically, the species-specific glycolipid antigens of *mycoplasma* can be detected by ionization using any ionization (EI method, ESI method, LSI method, FAB method, MALDI method, and the like) and acquiring a mass spectrum according to procedures of usual mass analysis method, and can be quantitated using a quantitation standard.

For example, in a case of *Mycoplasma fermentans*-specific glycolipid antigen GGPL-I, unique ion peaks are detected at 924, 896, 658, 640, 420, 402, 328, 310, 184, or 104 m/z of the mass charge ratio in a positive mode, and unique ion peaks are detected at 908, 880, 809, 642, 624, 404, 386, 312, 294, or 168 m/z of the mass charge ratio in a negative mode. Especially, among these peaks, the peak at 896 m/z is a characteristic peak of GGPL-I, and thus identification of existence of 896 m/z peak can be identification of existence of GGPL-I. For further exact identification, the existence of the multiple peaks described above is identified. In a case of *Mycoplasma fermentans*-specific glycolipid antigen GGPL-III, unique ion peaks are detected at 184, 239, 1049, or 1077 m/z of the mass charge ratio in a positive mode, or at 809, 823, 864, 988, 1047, or 1075 m/z of the mass charge ratio in a negative mode. Especially, among these peaks, the peak at 1049 m/z is a characteristic peak of GGPL-III, and thus identification of existence of 1049 m/z peak can be identification of existence of GGPL-III. On the other hand, the positive mode of *Mycoplasma pneumoniae*-specific glycolipid antigen GGL can be clearly observed with addition of sodium, and the unique peaks thereof appear at locations of 185, 202, 347, 363, 405, 497, 525, 659, 687, 915, or 943 m/z of the mass charge ratio, and appear at locations of 379, 635, 663, 891, or 919 m/z of the mass charge ratio in a negative mode. Especially, among these peaks, the peak at 915 m/z is a characteristic peak of GGL, and thus identification of existence of 915 m/z peak can be identification of existence of GGL (Herein, the positive mode means that test subject molecules are ionized with positive ion in a mass analyzer, and the negative mode means that test subject molecules are ionized with negative ion.).

Then, in order to quantitate amounts of these specific glycolipid antigens, a deuterated glycolipid that corresponds to at least one of these specific glycolipid antigens such as GGPL-I, GGPL-III and GGL Glc-type, GGL gal-type, is synthesized, and glycolipid standards having gradual concentrations are adjusted. Then, the lipid standards of each concentration are added to a test sample and measurement by a mass spectrum is performed. The height of the characteristic peak of the test sample is compared with the height of the unique peaks of the glycolipid standards, and when the two are in a comparable level of the height of the peak, the concentration of the glycolipid standard is adopted as the amount of the specific glycolipid antigen in the sample. For example, in Example 15, the amount of specific lipid antigen GGL extracted from $10^7$ cfu of cultured *Mycoplasma pneumoniae* bacteria is determined to be less than 50 pmol and more than 5 pmol from comparison of the height of the characteristic peak with the concentrations of the quantitation standards.

An actual sample from a test blood and the like includes not only extremely large amount of protein, but also blood cells, other bacteria, and the like in addition to lipid components, and thus needs pretreatment. Specifically, an actual sample is centrifuged using a solvent system in which water is added to an organic solvent such as methanol and chloroform, whereby to remove proteins contained in a large amount in the sample, and lipid fractions including lipid antigens is extracted as a lower layer. Furthermore, the lipid fractions can be separated and purified using chromatography with use of an adsorption carrier such as silica gel, or an affinity column with use of antibody with respect to targeted specific lipid antigen, and the like.

Using LC-MS that is a mass spectrometer having a function of a liquid chromatography (LC), separation of a lipid antigen and mass measurement can be carried out at the same time.

(6-5) Monitoring by Variation of Lipid Antigen Amount by a Mass Spectrum, and Optimization of Dosage Amount The lipid antigen particles of the present invention are administered as a vaccine to a *mycoplasma*-infected patient or infected animal, and then after a lapse of certain time, or temporally, specific lipid antigen amount in the patient- or animal-derived sample is measured by the method described above (6-4). When the "sample" is mentioned in the present invention, it includes body liquids, for example, the whole blood, the plasma, the serum, the joint fluid, the spinal fluid, the salivary juice, the amnionic fluid, the ascites fluid, the pleural effusion, the urine, the sweat, the pancreatic fluid, the synovial fluid, etc., and a tissue, a cell and the like, which are collected from a subject patient or animal. With such easy measurement method, a *mycoplasma* lipid antigen surviving in a sample such as the serum can be directly detected and quantitated, and thus it has an advantage that effects of the vaccine to a patient are quickly checked. Then, by monitoring temporal variation of the amount of the lipid antigens, inhibition activity for *mycoplasma* growth depending on the dosage amount and the administration time can be exactly evaluated, and then optimal treatment plan can be determined.

In other words, a treatment method in which administration of a vaccine preparation including the lipid antigen particles of the present invention is carried out along with monitoring of the lipid antigen amount variation by a mass spectrum and the like, demonstrates the greatest advantage as an individual treatment method for an individual *mycoplasma*-infected patient.

7. Regarding Vaccine Activity or Adjuvant Activity Including Bacterium-Mimic Particles (7-1) Regarding Vaccine The term "vaccine" mentioned in the present specification means a substance that can cause immune response, and is used as a wide meaning including a preventive vaccine for *mycoplasma* infection diseases by *mycoplasma* infection, and a therapeutic vaccine for *mycoplasma* infection. A vaccine is formulated and administered to animals such as human, domestic animals, and pets. In the formulation or administration, pharmacologically acceptable various excipients are suitably used similarly to a conventional vaccine preparation.

(7-2) Vaccine Function of *Mycoplasma*-Mimic Particles

Conventionally, as a vaccine for a pathogenic bacterium such as mycoplasmas, fungus body extract components, an inactivated vaccine, and the like were mainly used, and recently, a DNA vaccine, a synthetic peptide vaccine, and the like were also used. The vaccine containing the *mycoplasma*-mimic particles used in the present invention uses those separated and purified from each *mycoplasma* species-specific lipid antigen. Particularly, a synthetic lipid antigen by a chemical method and the like, which is similar to natural lipid antigen, is preferably used since it has controlled impurity and high safety.

Such *mycoplasma*-mimic particles are administered to a model animal, and as a result, it could be found out that the *mycoplasma*-mimic particles had a vaccine function that caused extremely high immune response. Particularly, in Example 5, when the *mycoplasma*-mimic particles were administered in advance for prevention to a rheumatoid arthritis model rabbit, revolutionary results are obtained in which the joint lesion was suppressed (FIG. 10).

In addition, since the specific lipid antigen itself has adjuvant activity as described in (7-3) below, there is a merit that the specific lipid antigen does not need an adjuvant that has many problems such as adverse effects.

(7-3) Adjuvant Function of the *Mycoplasma*-Mimic Particles

As the functions of the "adjuvant", the *mycoplasma*-mimic particles have two roles: increase of incorporation of antigen into a dendritic cell and activation of the dendritic cell.

As an adjuvant for a component vaccine, for example, an adjuvant using a mineral oil such as Freund complete adjuvant and Freund incomplete adjuvant, in which mineral oil is mixed with killed fungus body of *tuberculosis bacterium*, a phosphate aluminum adjuvant, or an inorganic adjuvant such as Alum adjuvant, which has aluminum hydroxide as a main component, and the like are known.

An adjuvant that has high functional effects, and is currently approved for many vaccines as an efficacious adjuvant is only aluminum hydroxide gel called Alum, but it has many problems in a point of adverse effects. A new adjuvant that has high efficacy and small adverse actions is pursued.

The *mycoplasma*-mimic particles of the present invention are found to have these 2 kinds of adjuvant functions (FIGS. 14 and 16), and are greatly expected as an adjuvant having high efficacy and small adverse actions.

An adjuvant is desired to have lower toxicity for human or an animal to be inoculated, and a *mycoplasma* synthetic antigenic lipid may be used as a new adjuvant for a component vaccine having no toxicity. The lipid antigen-containing microorganism-mimic liposome of the present invention has adjuvant activity for immune induction, and has low toxicity and low antigenecity itself, and thus can be used as an adjuvant for an antigen such as a vaccine and the like with respect to human. Particularly, when target antigen or immunogen is entrapped into the liposome, a strong vaccine is obtained. The synthetic lipid antigen is found out to effectively induce immunity, and thus can be used as an adjuvant having adjuvant activity for a liposome preparation.

Figure 15:
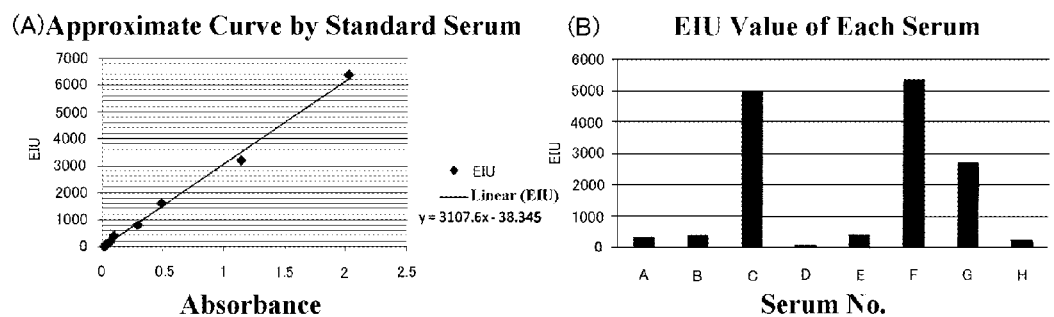
FIGS. 15(A) and 15(B) represent the serum antibody titer in the serum of a patient of a respiratory disease including *mycoplasma* pneumonia: IgA measurement results by ELISA method using *Mycoplasma pneumoniae*-specific antigen GGL Glc-type. It was found out that IgA antibody was induced in the human serum, and could be a mucosal immunity adjuvant.

In addition, as an index of cellular immunity with regard to a cellular immune adjuvant, delayed type allergy (DTH) reaction (TH1 cell in charge) in a mouse can be adopted. A target adjuvant can induce DTH reaction. Consequently, the *mycoplasma*-mimic particles of the present invention can be used as an adjuvant for a defense vaccine against pathogenic body infection, or an immunotherapy agent or a cancer immunotherapy agent thereof, with which TH1 cell is involved. In the present invention, it is found out that IgA is induced in the serum of a *mycoplasma*-infected patient, and it is revealed that an antigen thereof has actions on the mucosal immunity (FIG. 15). Particularly, the *mycoplasma*-mimic particles of the present invention can be an adjuvant that specifically activates mucosal immunity of influenza and the like.

The immunity encompasses humoral immunity and cellular immunity, and in addition thereto, lipid antigen immunity represented by natural killer T cell, which is located between the humoral immunity and the cellular immunity. Alum induces humoral immunity relatively well, but is considered not to be very effective for cellular immunity (Patent Document 27). The cellular immunity and natural immunity are considered to be important in prolonged virus or infection, but an adjuvant that is efficacious therefor does not advent. The *mycoplasma* synthetic lipid antigen particles of the present invention have such adjuvant activity.

8. Preparation of Vaccine for Prevention or Treatment of *Mycoplasma* Infection, and Protocol for Treatment (8-1) Vaccine for Prevention or Treatment of *Mycoplasma* Infection From lipid antigen-containing *mycoplasma*-mimic particles, which were prepared by simulating a form that exists on the membrane surface of *mycoplasma* (microorganism) and has action on the immune system, induction of specific antibody and vaccine activity were obtained.

With respect to two *Mycoplasma pneumoniae*-specific lipid antigens and two *Mycoplasma fermentans*-specific lipid antigens, relationship between *mycoplasma* infection and the progression of medical conditions are investigated for chronic intractable diseases (asthma, COPD, multiple sclerosis, rheumatic disease, and the like) using an antibody assay method, and patients affected due to *mycoplasma* infection are selected. For the selected patients, *mycoplasma* infection treatment also including effects of an anti-*mycoplasma* drug is performed. The term, treatment method, is a collective term of a lipid antigen vaccine, a lipid antigen antibody therapy, immunotherapy associated with a lipid antigen, an anti-bacterial agent or oriental medicine that reduces the amount of a lipid antigen, an anti-allergic agent that alleviates actions of a lipid antigen, a steroid agent, and the like, or a combination thereof. Herein, a diagnosis-treatment system using ELISA method is provided.

(8-2) Dosage Form and Administration Method

For the administration method, medical conditions are grasped using ELISA method, or a monitoring marker or a diagnosis method based on a *mycoplasma* lipid antigen, and administration method can be selected so as to correspond to the medical conditions of *mycoplasma* infection.

An administration route of the *mycoplasma*-mimic particles vaccine may be any one of intranasal, intradermal, subcutaneous, intramuscular, interperitoneal, intravenous, or oral administration. At the time, excipients such as a stabilizer, an antioxidant, a preservative, a stabilizer, a wetting agent, a lubricant, an emulsifier, a salt having an influence on osmotic pressure, a colorant, an alcohol, and a buffer, which are used in a conventional vaccine preparation, and pharmacologically acceptable, may be used in combination. In addition, the vaccine of the present invention may be used in a mixture with other antigen components, and may be concomitantly used with medicines such as an anti-bacterial agent such as known *mycoplasma* antibiotics, and an anti-inflammation agent.

In addition, the vaccine of the present invention can be expected not only for therapeutic effects, but also for preventive effects, and thus when *mycoplasma* infection is doubted, the vaccine of the present invention may be administered in advance, whereby to be effective as a preventive vaccine.

(8-3) Dosage Amount

The lipid antigen-containing bacterium-mimic particles of the present invention may be administered by single or repetitive administration in an amount efficacious to defense against *mycoplasma* infection, i.e., an amount for inducing immunity against the infection in human and animals.

When the lipid antigen-containing bacterium-mimic particles of the present invention is used in prevention and/or treatment for *mycoplasma* infection, the amount of the specific lipid antigen depends on subject animal, but is administered in a range of 1 μg to 1000 mg each time. The amount of the specific lipid antigen is 1 μg to 200 μg/each time for a small animal such as mouse, which is sufficiently effective, but is preferably administered to human in 100 μg to 100 mg/each time. Furthermore, the amount of the specific lipid antigen can be optimized using the evaluation method described above and the like depending on the administration methods such as the dosage amount, the administration timing, the administration number of times, and the administration area, and the respective use (for example, FIG. 24).

(8-4) Evaluation Method

Figure 17:
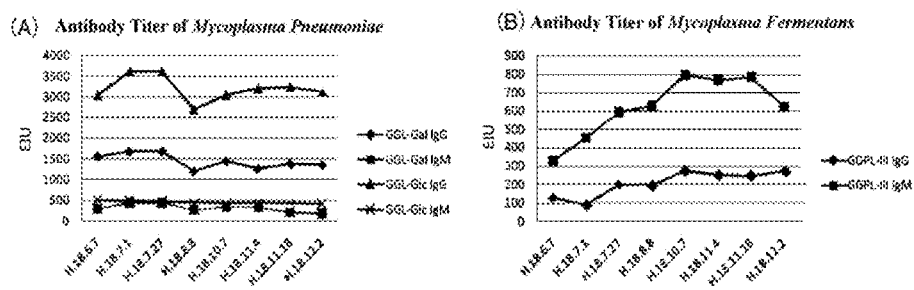

As shown in FIGS. 17 and 18, the synthetic lipid antigen particles are administered as a vaccine, and then the *mycoplasma*-specific antibody titer in the serum is measured using ELISA method that is as used for patients associated with *mycoplasma* infection, and effects of the vaccine can be judged by increase of the antibody titer. In addition, therapeutic effects by the vaccine administration can be evaluated by quantitatively directly measuring the amount of the *mycoplasma* species-specific glycolipid antigen with a mass spectrum.

Particularly, a method in which a vaccine and/or other medicines for *mycoplasma* is administered to a *mycoplasma*-infected patient or animal, and after a lapse of a certain time, or with time while repeating multiple administrations, the specific lipid antigen in the patient or animal-derived sample (serum and the like) is detected and/or quantitated with the mass analysis method described above (6-4), and the variation with time of the lipid antigen amount is monitored, allow easy, quick, and exact evaluations for the dosage amount of an administered vaccine and/or therapeutic agent, and effects of the treatment method itself such as administration time with respect to a subject *mycoplasma*-infected patient or animal for treatment, and thus is suitable in determination of an optimal treatment plan appropriate to individual patient or animal along with reconsideration of the treatment plan.

There are many patients of *mycoplasma* infection that becomes chronic and severe, and complicating diseases occur together, which makes it often unclear whether the cause of the disease is *mycoplasma* infection or not. Therefore, in fact, along with evaluation of effects of the vaccine administration, a plan for the next administration will be made. Hereinafter, a specific example of a protocol of diagnosis, prevention, and treatment will be shown.

(8-5) Protocol of Diagnosis, Prevention, and Treatment for Juvenile Pneumonia *Mycoplasma* (FIG. 20)

In the area of juvenile *mycoplasma* pneumonia, of course, early selection of an anti-bacterial agent by early specific quantitative diagnosis is an essential aspect, and thus accurate treatment policy is made, and appropriate switch by the diagnosis method to an anti-bacterial agent is expected.

Administration of a liposome that is the *mycoplasma*-mimic particles as a preventive vaccine inhibits *mycoplasma* infection. *Mycoplasma* is a cause of a severe disease such as juvenile meningitis, which can be prevented by the liposome. In addition, *mycoplasma* is also considered as a cause of diseases that undergo rapid progression, such as Kawasaki disease (Non-patent Document 30), but in that case, an antibody medicine is considered to be effective.

(8-6) Protocol of Diagnosis, Prevention, and Treatment for Adult *Mycoplasma* Pneumonia (FIG. 21)

It is understood that multiple *mycoplasma* species are involved in a cause of *mycoplasma* pneumonia. However, by antibody assay method using *Mycoplasma pneumoniae* species-specific and *Mycoplasma fermentans* species-specific lipid antigens, relationship between *mycoplasma* infection and the progression of medical conditions is already investigated for chronic intractable diseases (asthma, COPD, multiple sclerosis, rheumatic disease, cancer, and the like), and patients affected due to *mycoplasma* infection are selected (FIGS. 17 and 18). For the selected patients, *mycoplasma* infection treatment also including effects of an anti-*mycoplasma* drug is performed. *Mycoplasma* species-specific antibody titer is measured using ELISA method, or the amount of *mycoplasma* species-specific glycolipid antigen is measured by mass spectrometer and the like, whereby to suggest a diagnosis-treatment system from the titers, and further provide a preparation that adopts the glycolipid antigen as an antibody medicine or vaccine.

(8-7) Protocol of Diagnosis, Prevention, and Treatment for Chronic *Mycoplasma* Infections Such as Autoimmune Diseases (FIG. 22)

The vaccine preparation containing the *mycoplasma*-mimic particles of the present invention is administered while monitoring (diagnosis) of a chronic disease is performed using lipid antigens of *Mycoplasma pneumoniae* and *Mycoplasma fermentans* by an anti-lipid antigen antibody assay method (ELISA method) or a measurement method for *mycoplasma* species-specific lipid antigen amount (mass analysis method and the like).

(8-8) Diagnosis, Prevention, and Treatment for *Mycoplasma* Infection in Domestic Animals Such as a Pig (FIG. 13)

The *mycoplasma*-mimic particles of the present invention lead to prevention of pneumonia and improvement of yield efficiency. The *mycoplasma*-mimic particles of the present invention have adjuvant effects, and can possibly reduce or eliminate the use amount of an adjuvant such as mineral oil. The subject may be any kinds of animal such as a pig, a chicken, a cow, and vegetables. As the microorganism, a microorganism having pathogenicity as lipid antigen syndrome such as *mycoplasma, tuberculosis bacterium, Chlamydia*, and the like may be considered in similar method.

With respect to vaccines of *Mycoplasma* hyopneumoniae currently marketed against pig's *mycoplasma* pneumonia, adverse effects such as vitality loss by shock or fever in an allergy-like reaction are also reported. Identification of a causative substance in these vaccines is difficult as long as they use a fungus body including various components. In addition, a culture fluid used in culture of *Mycoplasma* hyopneumoniae fungus body is expensive since the culture fluid often includes a horse serum, a pig serum, and high protein components. Therefore, production cost is high, and frequent inoculation of such vaccine containing a high amount of proteins increases incidence of adverse effects such as allergy. Consequently, it was desired to specify only components associated with pulmonary lesion formation among structural components of fungus body of *Mycoplasma* hyopneumoniae, and to provide a vaccine containing only such components (component vaccine). *Mycoplasma* hyopneumoniae-specific bacterium-mimic particles contain no protein if an antigen is artificially synthesized, and thus allows development of an inexpensive, safe vaccine.

9. Other Use of the Bacterium-Mimic Particles

Immunological functions of the *mycoplasma*-mimic particles of the present invention include vaccine activity, antibody induction activity, cellular immunity induction activity, adjuvant activity, phagocytosis activity into macrophage, assimilation into an antigen presenting cell and functions as antigen presenting particles, and can act on mechanisms involved in immune function control such as activation of NKT cell, T cell, or B cell, and the use is broad by the present preparation that is safe, stable, and effective.

Particularly, many of virus (influenza, rotavirus, and the like) or bacteria that cause pneumonia, diarrhea, and the like enter a living body through a mucosal membrane such as a respiratory organ or digestive organ. If the immune reaction of the mucosal membrane, which is the entrance route, can be enhanced, it is possible to fight off these microorganisms effectively. The *mycoplasma*-mimic particles of the present invention, which can be expected to have adjuvant effects that can induce mucosal immunity, i.e., IgA, can enhance effectively the immunity with respect to such microorganism antigens by immunization with incorporation of antigens of these microorganisms. Furthermore, at the same time, the *mycoplasma*-mimic particles of the present invention can be expected to have vaccine effects for *mycoplasma* infection. It is known that *mycoplasma* and influenza infection or *pneumococcus* can be infected at the same time to exacerbate medical conditions, and the *mycoplasma*-mimic particles of the present invention can be used as a mixed vaccine having high safety.

In addition, the *mycoplasma*-mimic particles of the present invention can be also used as a liposome preparation for "DDS" for administration of an anti-bacterial agent, an anti-virus agent, and the like into a living body.

10. Miscellaneous

Other terms and concepts in the present invention will be specifically prescribed in explanation of the present invention embodiments or Examples. The terms are basically in accordance with IUPAC-IUB Commission on Biochemical Nomenclature, or on the basis of the meanings of conventionally used terms in the field. In addition, various techniques that are used for the purpose of implementing the present invention can be easily and certainly implemented by a person skilled in the art on the basis of a known document and the like except a technique for which the source is indicated particularly. For example, genetic engineering and molecular biology technique can be carried out by the methods described in J. Sambrook, E. F. Fritsch & T. Maniatis, "Molecular Cloning: A Laboratory Manual (2nd edition)", Cold Spring Harbor Laboratory Press, Cold Spring Harbor, N.Y. (1989); D. M. Glover et al. ed., "DNA Cloning", 2nd ed., Vol. 1 to 4, (The Practical Approach Series), IRL Press, Oxford University Press (1995); Ausubel, F. M. et al., Current Protocols in Molecular Biology, John Wiley & Sons, New York, N.Y., 1995; Edited by The Japanese Biochemical Society, "Sequel Biochemistry Experiment Lecture 1, Gene Research Method II", Tokyo Kagaku Douj in (1986); Edited by The Japanese Biochemical Society, "New Biochemistry Experiment Lecture 2, Nucleic acid III (recombinant DNA technique)", Tokyo Kagaku Doujin (1992); R. Wu ed., "Methods in Enzymology", Vol. 68 (Recombinant DNA), Academic Press, New York (1980); R. Wu et al. ed., "Methods in Enzymology", Vol. 100 (Recombinant DNA, Part B) & 101 (Recombinant DNA, Part C), Academic Press, New York (1983); R. Wu et al. ed., "Methods in Enzymology", Vol. 153 (Recombinant DNA, Part D), 154 (Recombinant DNA, Part E) & 155 (Recombinant DNA, Part F), Academic Press, New York (1987), and the like, or by the methods cited in the description of the documents there, or by methods substantially similar to those described above or methods modifying those described above. In addition, various proteins, peptides, or DNAs that encode them that are used in the present invention are available from an existing data base, for example from the National Center for Biotechnology Information.

EXAMPLES

Hereinafter, the present invention will be further specifically explained in details with Examples, but is not limited to Examples below.

The descriptions in the technical documents, the patent publications, and the specifications of patent applications cited in the present specification are referred as descriptions of the present invention.

Example 1

Preliminary Experiment for Preparation of Pathogenic *Mycoplasma*-Mimic Particles (1-1) Optimization of Particle Size of Liposome Particles 15.46 mg of Lipid, which was extracted and purified from *Mycoplasma hyopneumoniae* cultured in a large amount, and 3.31 mg of high purity cholesterol of a marketed product (manufactured by NOF CORPORATION) were dissolved in 600 µl of ethanol, and the solution was added to 3 ml of 8.5% sucrose solution in 60° C. constant-temperature bath and treated with ultrasonic wave for 3 minutes (ultrasonic wave washing machine US-104 manufactured by SND Co., Ltd.) to prepared liposome particles. The particle diameter was measured with an apparatus for measurement of the Zeta potential, the particle diameter, and the molecular weight (ZETASIZER nano series manufactured by Malvern Instruments Ltd) and uniformed to about 100 nm (FIG. 4).

(1-2) Investigation of Composition of *Mycoplasma*-Mimic Liposome Particles

To a constant amount of synthetic GGPL-III, dipalmitoyl phosphatidylcholine (DPPC) (manufactured by NOF CORPORATION) and cholesterol (manufactured by NOF CORPORATION) with various ratios changed were added, and the mixtures were dissolved in a chloroform-methanol solution, and concentrated and dried. To a dried sample, RPMI-1640 (manufactured by SIGMA), which is a medium for cell culture, was added, and treated with ultrasonic wave at 25° C. for 40 minutes. The particle diameter of the sample was measured with an apparatus for measurement of the Zeta potential, the particle diameter, and the molecular weight (ZETASIZER nano series manufactured by Malvern Instruments Ltd) (FIG. 23).

The fatty acid of phosphatidyl choline used was a fatty acid of 16-carbon number saturated type, which is a most typical form of natural *mycoplasma*, and was prepared as liposome particles along with a *mycoplasma* lipid antigen in various ratios of the fatty acid to cholesterol, and particle diameters and the distribution thereof were measured. From these results, it was found out that a molar ratio of 10-50% lipid antigen, 20-50% phosphatidyl choline, and 10-50% cholesterol was preferable. These results were close to the analysis data of the *mycoplasma* lipid (Non-patent Document 29).

(1-3) Quality Control of Lipid Antigen

Measurement of HPLC was carried out under following conditions: Column: Waters C4 1.0×150 mm, mobile layer: 100% methanol, injection amount: 5 µl, flow rate: 0.05 ml/min, temperature: 40° C. (inside, outside), detector: evaporation light scattering detection (ELSD), and UV (215 nm) (all manufactured by Waters).

The relationship between each GGPL-III concentration and the peak area thereof was plotted to a graph. As a result, the peak area increased dependently on the GGPL-III concentration. Each standard curve was shown in the figures. From the results described above, it is considered that evaporation light scattering detection (ELSD) is suitable in detecting GGPL-III by HPLC analysis (FIG. 5) due to the fact that the dynamic range at peak area is wide in ELSD.

For the mass analysis, each sample was dissolved in 500 µl of a solution of chloroform: methanol (2:1), and 1 µl of the solution was diluted to 10000 folds with methanol. 1 µl of the diluted sample was applied to the target. Furthermore, 1 µl of a matrix solution (2,5-hydroxybenzonic acid and sodium trifluoroacetate) was applied to the target, and measured with a mass analysis apparatus (autoflex II TOF/TOF manufactured by BRUKER). From the results of the mass analysis, it was found out that the lipid antigen had high purity (FIG. 5).

Example 2

Antibody Induction of *Mycoplasma pneumoniae*-Synthetic Lipid Antigen

Using *Mycoplasma pneumoniae*-synthetic lipid antigen (GGL Glc-type), *Mycoplasma pneumoniae*-mimic particles were prepared by the same method as in Example 1 (1-2). The synthetic GGL Glc-type can be synthesized by the method described in Patent Document 8 and the like.

Figure 7:
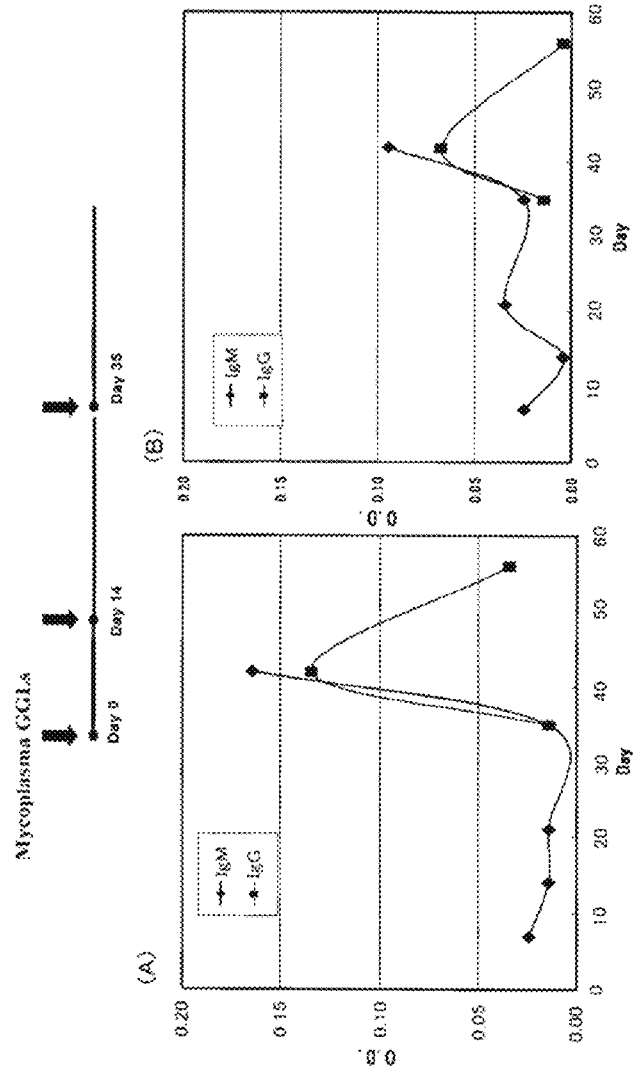
FIGS. 7(a) and 7(b) each represent induction of IgG and IgM antibody using the *Mycoplasma pneumoniae*-mimic particles interperitoneally administered to a mouse.

Using the mimic particles, two C57BL/6 mice were immunized. Specifically, 100 µl of the solution containing the particles was inoculated to the mice interperitoneally three times (Day 0, Day 14, and Day 35), and the blood was collected from the mice, and IgG and IgM antibody titers of each sample were measured with an enzyme antibody immune method (ELISA method). As a result, as shown in FIG. 7, IgG and IgM antibody could be induced in the two mice.

These results show that the GGL Glc-type liposome particles can work as *mycoplasma*-mimic particles, and induce specific antibody in vivo.

Example 3

Specific Antibody Induction by *Mycoplasma fermentans*-Mimic Particles (Synthetic GGPL-III)

500 µg of *Mycoplasma fermentans*-synthetic GGPL-III was added with 1 ml physiological saline, and treated with ultrasonic wave for 30 minutes, whereby to form liposome particles. The particles were interperitoneally inoculated to a mouse model SKG mouse which naturally develops chronic rheumatoid arthritis. 4 days after the inoculation, the blood was collected, and inhibition activity of the blood for growth of *Mycoplasma fermentans* was measured with a metabolism inhibition test.

The results show that antibody against the *mycoplasma* lipid antigen in the mouse serum can be specifically induced, and show antibody titers depending on the dilution degree particularly in a case of IgG. In addition, it was also found out that growth of *mycoplasma* was suppressed (FIG. 8).

These results show that GGPL-III liposome particles work as *mycoplasma*-mimic particles, and can induce specific antibody in vivo.

Example 4

Preparation of *Mycoplasma fermentans*-Infected Animal Model

Viable bacteria of *Mycoplasma fermentans* were inoculated to a rabbit (Newzealand White, male, about 2 kg) transtracheally, to prepare a pneumonia model rabbit, and were inoculated to a rabbit trans-knee articularly in the same manner to prepare a rheumatoid arthritis model rabbit. In Experiment 1, an amount of $10^9$ CFU/rabbit was inoculated singly on Day 0, to prepare two pneumonia model rabbits and three arthritis rabbits. In Experiment 2, an amount of $10^9$ CFU/rabbit was inoculated respectively three times in total on Day 0, Day 7, and Day 21, to prepare three pneumonia model rabbits and three arthritis rabbits. Among these model rabbits, rapid increase of IgG antibody titer of blood GGPL-III was observed in 4/6 examples (FIG. 9).

From these results, it was proved that *mycoplasma* causes not only pneumonia, but also many chronic inflammatory diseases (FIG. 1) that lead to arthritis. In addition, in Example 5, similarly produced model rabbits are used in the evaluation of the vaccine activity.

Example 5

Vaccine Effects in *Mycoplasma fermentans*-Infected Animal Model

*Mycoplasma fermentans*-mimic particles were prepared using synthetic *Mycoplasma fermentans* lipid antigen (GGPL-III) in the same method as in Example 1 (1-2).

*Mycoplasma fermentans*-infected rheumatoid arthritis model was prepared in the same method as in Example 4 described above. When immunization was performed with *Mycoplasma fermentans*-mimic particles interperitoneally to the rabbits four times before the preparation of the *Mycoplasma fermentans*-infected rheumatoid arthritis model, the joint lesion of the *Mycoplasma fermentans*-infected rheumatoid arthritis model was suppressed. From these results, it was proved that the synthetic GGPL-III *Mycoplasma fermentans* lipid antigen particles become an immunotherapeutic agent such as a vaccine. This corresponds to priming effects for immunity functions of the synthetic lipid antigen (FIG. 10).

These results show that the *mycoplasma*-mimic particles (GGPL-III) of the present application can be a preventive vaccine for an rheumatoid arthritis disease caused by *mycoplasma* infection.

Example 6

Figure 11:
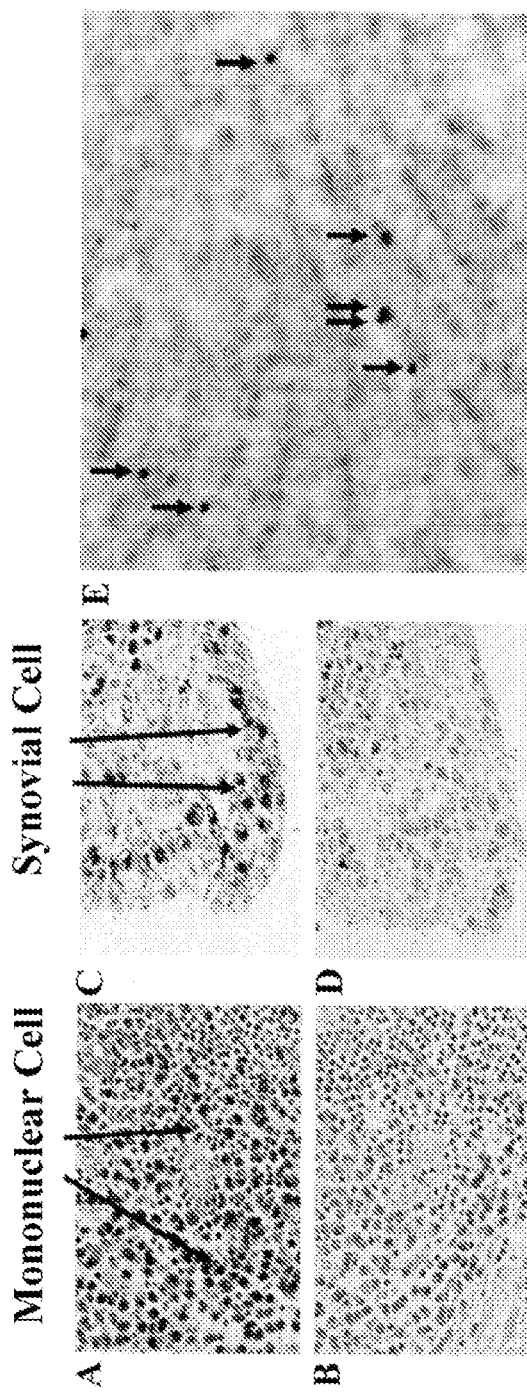
FIGS. 11 (C) and 11 (D) show the immunohistochemical staining of the tissue containing synovial cells. The arrow heads in FIG. 11(C) show the representative positively stained synovial cells. Anti GGPL-III antibody was used as a primary antibody.

Distribution of *Mycoplasma fermentans*-Lipid Antigen (GGPL-III) in Rheumatoid Arthritis Patient-Derived Synovial Cell: (FIG. 11)

Method 1: Immunostaining
Synovial cells were separated from a patient of rheumatoid arthritis, and stained with anti-GGPL-III antibody and IgM of a negative control mouse.
Method 2: Immunoelectron Microscopy
Synovial cells were separated from a patient of rheumatoid arthritis, and detection of GGPL-III was performed with anti-GGPL-III antibody as a primary antibody and with IgG and IgM attached with gold colloid as a secondary antibody (by the method of Non-patent Document 31).

From the results (A to D) in the immune-staining method, and also from the results (E) in the immunoelectron microscopy, it was observed that *Mycoplasma fermentans*-specific lipid antigen (GGPL-III) increased in a significant amount in the synovial cell of the rheumatoid arthritis patient.

These results show that the lipid antigen is involved in a route of being incorporated into an immune cell, transported to a rough-surfaced endoplasmic reticulum, and antigen-presented (Non-patent Document 31) in *mycoplasma* infection. Specific B cells are further induced from the antigen-presenting cell, and antibody is produced. In addition, T cell or NKT cells that react specifically with a lipid antigen are induced.

Example 7

Measurement of IgA Using *Mycoplasma pneumoniae*-Specific Antigen GGL Glc-Type in the Serum of *Mycoplasma* Respiratory Disease-Affected Patient IgA in the serum of *mycoplasma* respiratory disease-affected patient was measured using ELISA with *Mycoplasma pneumoniae*-synthetic GGL Glc-type as an antigen. IgA antibody against *Mycoplasma pneumoniae* GGL Glc-type was recognized in the serum of the *mycoplasma* respiratory disease-affected patient. This suggested that *Mycoplasma pneumoniae* GGL Glc-type can be an adjuvant for mucosal immunity.

In an immune response, IgA is a subclass of an antibody produced from a mucosal immune system. Consequently, the fact that IgA is induced for the antigen means that the antigen has an action on the mucosal immunity. Consequently, these results showing that IgA antibody against the *mycoplasma*-specific lipid antigen is induced in human, show that the *mycoplasma*-mimic particles of the present invention have a strong action on the mucosal immunity. In consideration of the fact that the *mycoplasma*-mimic particles have an adjuvant action as one of the immune functions (Example 10), the *mycoplasma*-mimic particles can be an adjuvant that specifically activate mucosal immunity that is effective for influenza infection and the like.

Example 8

Cell Immunity Activity of the *Mycoplasma*-Mimic Particles

Mononuclear cells were separated from the peripheral blood of a healthy individual. A sample in which interleukin 2 and *mycoplasma*-mimic particles (GGPL-I, or GGPL-III) were added to the mononuclear cells, and a sample of the mononuclear cells with no addition of the *mycoplasma*-mimic particles were cultured, and supernatants thereof were recovered, and the amounts of interferon γ in the supernatant were measured with an enzyme antibody immune method (ELISA method).

Figure 16:
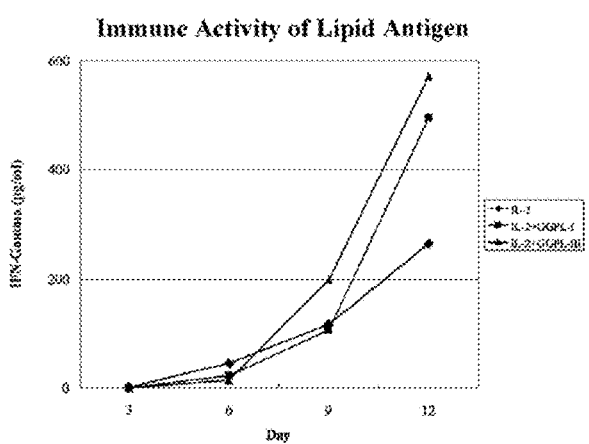
FIG. 16 represents cell immunity activity of the *mycoplasma*-mimic particles.

As a result, it was found out that the production amount of interferon γ increased by double or more in the administration of added *mycoplasma*-mimic particles (GGPL-I, GGPL-III) as compared with the administration of interleukin 2 alone (FIG. 16).

These results show that the *mycoplasma*-mimic particles of the present invention (GGPL-I and/or GGPL-III)) have cell immunity induction activity.

Example 9

Investigation of Disease for which the Vaccine of the *Mycoplasma*-Mimic Particles are Efficacious (9-1) Assay of Antibody Titer for *Mycoplasma pneumoniae* and *Mycoplasma fermentans* of Juvenile Rheumatoid Arthritis Patient with ELISA Method (FIG. 17)

This patient had cold symptoms. The patient had a pain and deformity on the finger joints after 1 to 2 months, and then visited a hospital after 3 months, and was diagnosed as juvenile rheumatoid arthritis. The patient received treatment with oral medicine, and the pain on the finger joint became less severe gradually. The antibody titers of *Mycoplasma pneumoniae* and *Mycoplasma fermentans* in the patient of juvenile rheumatoid arthritis were measured by ELISA method for the first about six months. As a result, it was proved that IgM antibody against *Mycoplasma fermentans*-specific GGPL-III clearly increased, and associated with *Mycoplasma fermentans* infection. In addition, from other examination results, it was found out that IgM antibody against *Mycoplasma fermentans*-specific GGPL-III increased to 8 folds in the results with conventional *mycoplasma* CF method, and the *mycoplasma* infection was negative, but *Mycoplasma fermentans* was detected in the blood with PCR, and *Mycoplasma fermentans* infected and existed in the blood. From the results described above, it could be proved that in initial development of juvenile rheumatoid arthritis of a patient, there is a patient whose actual cause of juvenile rheumatoid arthritis was *Mycoplasma fermentans* infection. For these patients, GGPL-III antibody titer was measured, whereby to confirm the infection. It is effective to administer the vaccine containing the *mycoplasma*-mimic particles (GGPL-III) of the present application as early as possible. That is to say, for some patients of juvenile rheumatoid arthritis that is conventionally unclear for the cause, a cause-specific treatment becomes possible, and thus the present vaccine containing the *mycoplasma*-mimic particles becomes a treatment method that leads to revolutionarily radical cure.

(9-2) Results of Measurement of Antibody Titers of *Mycoplasma pneumoniae* and *Mycoplasma fermentans* in Sarcoidosis Patient with ELISA Method In the same method, antibody titers of *Mycoplasma pneumoniae* and *Mycoplasma fermentans* were measured (FIG. 18).

This patient had a pain on the knees, and had a checkup in a hospital. The patient was recognized to have swelling in bilateral hilar lymph node and diagnosed as sarcoidosis. At the time, the antibody was in 160 folds with the *mycoplasma* PA method, which was a conventional examination method, and possibility of association with *mycoplasma* infection was considered. By treatments including antibiotics that are effective for *mycoplasma* infection, no pain on the knee joints continued until the pain on the knee joints reactivated from May, 2006. The antibody was in 80 folds with the *mycoplasma* PA method, and decreased as compared with that of previous time, but the pain on the knee joints became less severe by the same treatments as those of the previous time, i.e., treatments including antibiotics that are effective for *mycoplasma* infection. At the time of reactivation of the symptoms, IgG antibody against *Mycoplasma fermentans*-specific GGPL-III clearly increased, and the symptom became less severe by the treatments and the antibody titer decreased. From this, it was proved that the infection of *Mycoplasma fermentans* was associated.

From the results described above, it could be proved similarly that the actual cause was also *Mycoplasma fermentans* infection in patients of sarcoidosis at the time of this reactivation. Administration of the vaccine of the *mycoplasma*-mimic particles (GGPL-III) of the present application can be expected to be effective for this patient.

(9-3) Change of IgG and IgM Antibody Titers of *Mycoplasma pneumoniae* (GGL Gal-Type) in the Serum of Plural Multiple Sclerosis Patients (FIG. 19)

The antibody titers of GGL Gal-type antibodies (IgG and IgM) in the serum of multiple sclerosis patients were measured. From these results, it could be proved that the actual cause was also *Mycoplasma pneumoniae* infection in patients with multiple sclerosis. Due to the fact that an antibody against *Mycoplasma pneumoniae*-specific lipid antigen was induced, it was proved that this lipid antigen had vaccine activity. Multiple sclerosis is an intractable disease which is exacerbated by a year unit repeating aggravation and alleviation of the symptoms in a year. For this patient with multiple sclerosis, administration of the *mycoplasma*-mimic particles (GGL Gal-type) vaccine by the lipid antigen bacterium-mimic particles of the present application can be expected to be effective in therapeutic effects.

Example 10

Production of Interferon γ by *Mycoplasma*-Synthetic Lipid Antigen

Mononuclear cells were separated from the peripheral blood of a healthy individual. A sample in which interleukin 2 and *Mycoplasma fermentans*-synthetic lipid antigen GGPL-III were added to the mononuclear cells, and a sample of the mononuclear cells with no addition of the *Mycoplasma fermentans*-synthetic lipid antigen GGPL-III were cultured, and supernatants thereof were recovered, and the amounts of interferon γ in the supernatants were measured with an enzyme antibody immune method (ELISA method) and compared. The addition of the lipid antigen to interleukin 2 in human peripheral-blood mononuclear cell remarkably increased the production amount of interferon γ in comparison with the mononuclear cell with no addition of the lipid antigen (FIG. 16). These results show that the *mycoplasma*-mimic particles (GGPL-III) of the present application have cell immunity induction activity.

Example 11

Figure 14:
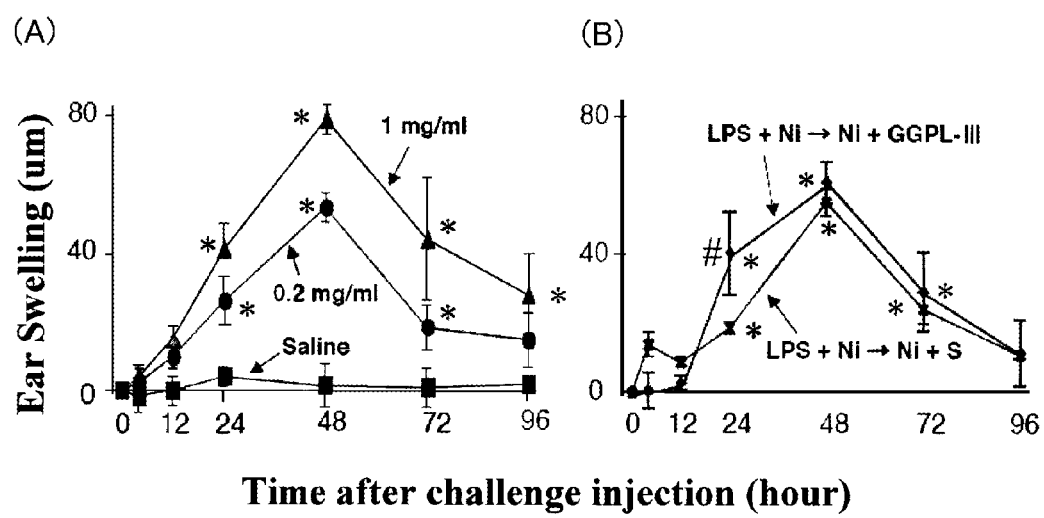
FIGS. 14(A) and 14(B) represent adjuvant effects of *Mycoplasma fermentans*-specific lipid antigen (GGPL-III).

Adjuvant Effects of *Mycoplasma fermentans*-Specific Lipid Antigen (GGPL-III) (FIG. 14)

As shown in FIG. 14(A), it was found out that administration of the *Mycoplasma fermentans*-mimic particles (GGPL-III) along with metal nickel (antigen) to the ears of a mouse had effects of enhancing antibody production performance dose-dependently (administrations of 0.2 mg/ml and 1 mg/ml). FIG. 14(B) shows that the *Mycoplasma fermentans*-mimic particles (GGPL-III) have equivalent cell immunity activity to that of LPS. In addition, the *Mycoplasma fermentans*-mimic particles (GGPL-III) have adjuvant activity that potentiates antigen activity. Lipid A developed by LPS started to be used as an adjuvant, but the *mycoplasma* lipid antigen can be also expected as an adjuvant.

Example 12

Vaccine Effects of the *Mycoplasma*-Mimic Particles Using Pig's *Mycoplasma* Hyopneumoniae-Specific Purified Lipid Antigen

*Mycoplasma hyorhinis* and *Mycoplasma hyopneumoniae* were cultured in a large amount, and fractionated with chloroform-methanol, and developed with a thin layer chromatography (chloroform:methanol:0.2% calcium chloride=55:45:10). After the development, the resultant was stained with immune-staining method using orcinol sulfuric acid, and detected (FIG. 13).

The *Mycoplasma hyopneumoniae*-mimic particles were prepared using the purified lipid antigens, and gave immunization to a mouse interperitoneally three times. The blood was collected on 4 days after the final inoculation, and inhibition activity for *mycoplasma* growth in the blood was measured with a metabolism inhibition test. As a result, it was found out that the *mycoplasma* growth was suppressed.

Example 13

Figure 12:
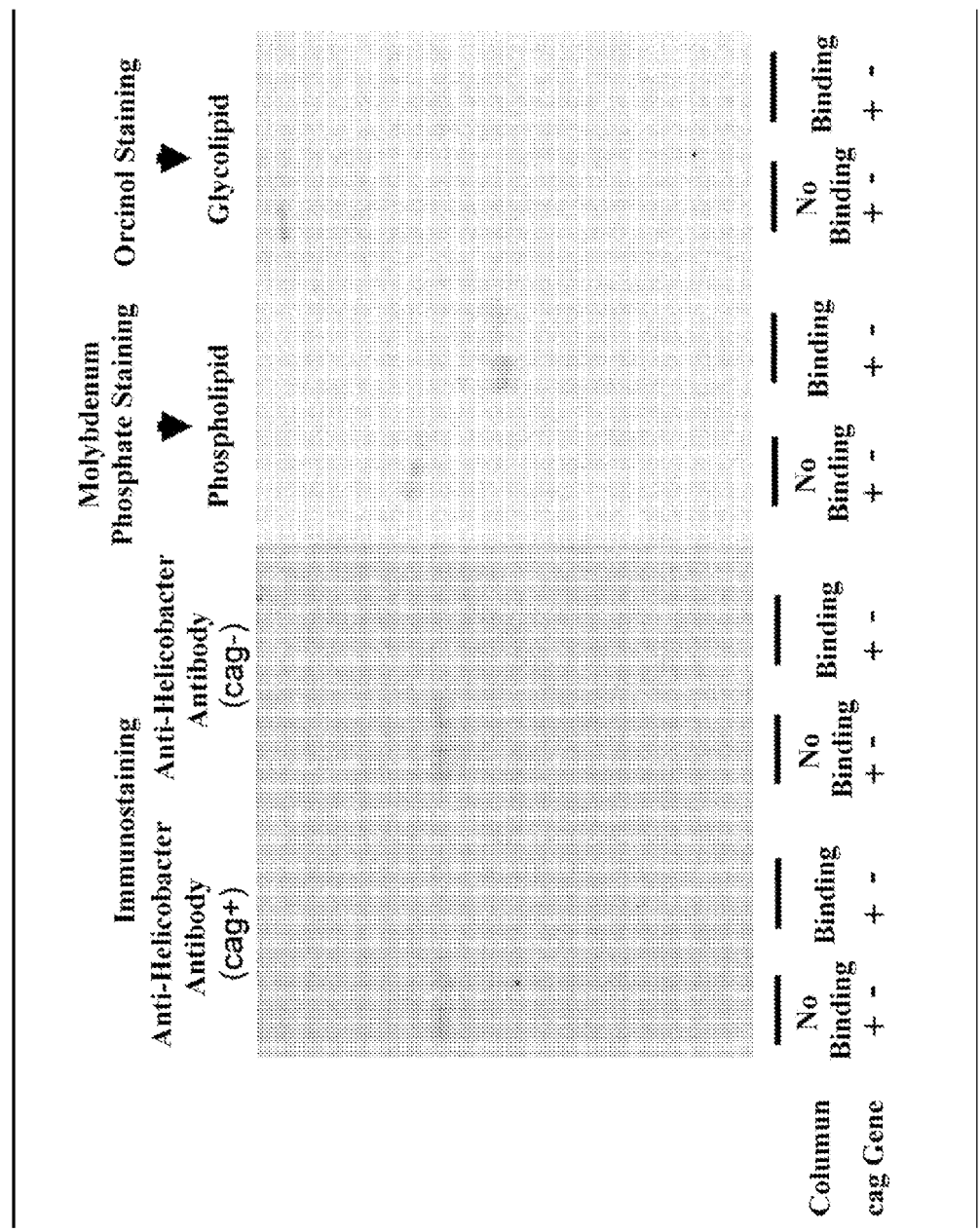
FIG. 12 represents a lipid antigen of *Helicobacter pylori* and interferon γ induction activities.

*Helicobacter pylori*-Specific Lipid Antigen and Detection Thereof (FIG. 12)

*Helicobacter pylori* was cultured in a large amount and fractionated with chloroform-methanol, and developed with a thin layer chromatography (chloroform:methanol:0.2% calcium chloride=60:28:3).

After the development, the specific lipid antigen was detected using molybdenum phosphate staining and immune-staining using orcinol sulfuric acid, whereby to recognize the *Helicobacter pylori*-specific lipid antigen.

Using the purified specific lipid antigen of *Helicobacter pylori*, *Helicobacter pylori*-mimic particles were prepared in the same method as in Example 1 (1-2). Using these *Helicobacter pylori*-mimic particles, production of interferon γ from bone marrow cells of the C57BL/6 mouse, the amount of interferon γ in the supernatant was measured with an enzyme antibody immune method (ELISA method). From these results, it was found out that the *Helicobacter pylori*-mimic particles of the present application had induction activity of interferon γ.

Example 14

Optimization of Administration Method of the *Mycoplasma*-Mimic Liposome Particles

*Mycoplasma pneumoniae*-mimic particles (GGL Glc-type), which were prepared in the same method as in Example 1 (1-2), were injected interperitoneally 4 times to 2 month-old mice (about 30 g body weight) divided into four groups in 200 μg, 50 μg, and 20 μg, respectively to give immunization. No antigen was administered to a control group. As shown in the lower part of FIG. 24, the blood was collected portionwise by 4 times, and each of the IgM antibody titers was measured with ELISA (the value is an average value for each group). The groups of 50 μg and 20 μg administrations showed high antibody titer beyond the cutoff value. However, the antibody titer does not rise in an administration group of such high concentration as 200 μg. Thus, it was found that the optimal dosage amount of *Mycoplasma pneumoniae*-mimic particles (GGL Glc-type) used in this Example was about 10 to 100 μg/each time, which was sufficiently effective. If human is supposed to be administered, the optimal dosage amount of *Mycoplasma pneumoniae*-mimic particles (GGL Glc-type) becomes about 100 μg to 10 mg/each time. This is within a range first supposed (about 1 μg to 200 μg/each time in a small animal such as a mouse), and optimization of the dosage amount can be conducted easily in such method in actual inoculation of the vaccine.

Example 15

Detection and Quantitation of *Mycoplasma* Species-Specific Glycolipid Antigen

In this experiment, for *Mycoplasma pneumoniae*-specific glycolipid antigen GGL, which is typical among *mycoplasma* species-specific glycolipid antigens, a model experiment was performed to check possibility of quantitation of the GGL amount contained in a sample such as the serum of a patient. Basic procedures were in accordance with those of the method of Patent Document 6.

That is to say, GGL was previously synthesized as a synthetic standard product corresponding to GGL, and further [H3]-GGL (d6-GGL) was synthesized as a quantitation standard, to which six deuterated [H3] were introduced.

On the other hand, *Mycoplasma pneumoniae* was cultured in a culture fluid, and the amount of the fungus body was quantitated by the colony number, which was a conventional method. The lipid antigen GGL was extracted, or separated and purified from $10^7$ cfu of the fungus body. A sample containing the $10^7$ cfu-cultured *Mycoplasma* pneumonia was well mixed with an organic solvent (0.8 ml) such as methanol:chloroform=1:1, and added with water (0.2 ml), and subjected to centrifuge procedure at about 2500 to 3000 g, whereby to cause layer separation. The lipid fraction containing target GGL(C16: 0) in the chloroform layer of the lower layer, was obtained as separated from proteins or blood cells. The lipid fraction was further purified using Iatrobeads (silica in which hydroxide groups are capped) by DIAION (manufactured by Mitsubishi Chemical Corporation).

In order to measure the amount of this lipid antigen, [H3]-GGL(C16: 0) was added to the lipid fraction described above in gradual concentrations, and each mass spectrum was measured in a positive mode by a mass analyzer (manufactured by Bruker Daltonics K.K.) with ionization by sodium addition (FIG. 25).

As a result, when the height of the characteristic peak (915 m/z) of target GGL (C16: 0) was compared with the height of the characteristic peaks (921 m/z) of [H3]-GGL (C16: 0) at the same time, it was found out that height of the characteristic peak (915 m/z) of target GGL (C16: 0) was interposed between the height of 50 pmol [H3]-GGL(C16: 0) addition and 5 pmol [H3]-GGL(C16: 0) addition. Thus, it could be determined that the abundance of GGL (C16: 0) was between 50 pmol and 5 pmol. In other words, it was found out that 50 pmol to 5 pmol of the *mycoplasma*-specific lipid antigen GGL (C16: 0) existed in $10^7$ cfu of the cultured *mycoplasma* fungus body in the model sample. In addition, these results also show that if about $10^5$ cfu of the fungus body exists, it can be sufficiently detected.

Consequently, it could be proved that the present technique is a technique that allows immediate determination of infection *mycoplasma* species in a case when the measurement is conducted using actual *mycoplasma*-infected, patient-derived tissue or blood, and allows accurate judgment of the degree of the infection, and also can be extremely effectively used in judgment of therapeutic effects after a vaccine therapy or chemotherapeutic agent therapy is performed, or during the progression of the therapy.

Example 16

Detection of *Mycoplasma fermentans*-Specific Lipid Antigen GGPL-III in Articular Tissue of Rheumatoid Arthritis Patient FIG. 11 is a figure showing that *Mycoplasma fermentans*-specific lipid antigen GGPL-III in the articular tissue of a rheumatoid arthritis patient is stained with specific antibody. This time, FIG. 11 shows that existence of GGPL-III in the articular tissue of a rheumatoid arthritis patient can be also detected with the method using a mass analyzer described in Example 15.

Lipid components were separated, purified, and obtained from the articular tissue of a rheumatoid arthritis patient by using Iatrobeads (DIAION, manufactured by Mitsubishi Chemical Corporation).

The fractions were analyzed by a mass analyzer (manufactured by Bruker Daltonics K.K.), and as a result, a peak at a location of 1049 m/z that represented existence of GGPL-III could be found out (FIG. 26).

Example 17

Analysis of Clinical Sample of *Mycoplasma* Infection-Suspected Patient

From multiple pneumonia patients suspected of *mycoplasma* infection, pharyngeal swab fluids were collected, and obtained eluted fractions were ionized and analyzed with a mass analyzer (manufactured by Bruker Daltonics K.K.) in the same method as in Example 16. As a result, peaks specific to *Mycoplasma pneumoniae*-specific glycolipid antigen GGL could be detected in multiple samples as shown in FIG. 27.

The invention claimed is:
1. *Mycoplasma*-mimic particles, comprising:
liposome particles including at least one *mycoplasma*-specific lipid antigen, a liposome-constituting lipid component and at least one other antigenic substance on the surfaces of the liposome particles,
wherein the antigenicity of each of the at least one other antigenic substance increases by adjuvant effects of the *mycoplasma*-specific lipid antigen.
2. The *mycoplasma*-mimic particles according to claim 1, wherein the at least one other antigenic substance is a virus-derived antigen peptide.
3. A method of suppressing or treating a disease caused by a *mycoplasma* infection, comprising:
a process of administering a vaccine for suppressing or treating of a disease caused by a *mycoplasma* infection at least once to human or an animal that is affected or suspected to be affected with the *mycoplasma* infection,
wherein the vaccine comprises *mycoplasma*-mimic particles as an active ingredient and a pharmaceutically acceptable excipient,
wherein the *mycoplasma*-mimic particles comprise liposome particles including at least one *mycoplasma*-specific glycolipid antigen as a liposome-constituting lipid component,
wherein the at least one *mycoplasma*-specific glycolipid antigen is chemically or enzymatically synthesized, and then separated and purified.

4. The method of treating a disease caused by *mycoplasma* infection according to claim 3, further comprising:
 measuring the amount of a *mycoplasma* species-specific lipid antigen or the amount of a lipid antigen-specific antibody before and/or after administration of the vaccine, and
 determining administration time and dosage amount of the next vaccine based on the measured value.

5. A vaccine for prevention or treatment of a disease caused by a virus infection, comprising: the *mycoplasma*-mimic particles according to claim 2 containing a virus-derived antigen peptide on the surface of the particles as an active ingredient and a pharmaceutically acceptable excipient.

6. The vaccine according to claim 5, wherein the virus is influenza virus and the disease is influenza.

7. A method of suppressing or treating a disease caused by a virus infection, comprising:
 administering the vaccine for suppression or treatment of a disease caused by a virus infection according to claim 5 to human or an animal that is affected or suspected to be affected with the virus infection disease.

8. The suppression or treatment method according to claim 7, wherein the virus is influenza virus and the disease is influenza.

9. The suppression or treatment method according to claim 3, wherein
 the disease caused by a *mycoplasma* infection is pneumonia, asthma, or rheumatic disease.

* * * * *